US007968595B2

(12) United States Patent
Cai et al.

(10) Patent No.: US 7,968,595 B2
(45) Date of Patent: Jun. 28, 2011

(54) SUBSTITUTED 4-ARYL-CHROMENE AS ACTIVATOR OF CASPASES AND INDUCER OF APOPTOSIS AND AS ANTIVASCULAR AGENT AND THE USE THEREOF

(75) Inventors: Sui Xiong Cai, San Diego, CA (US); John A. Drewe, Carlsbad, CA (US); Shailaja Kasibhatla, San Diego, CA (US); William D. Kemnitzer, San Diego, CA (US); Ben Y. Tseng, San Diego, CA (US); Charles Blais, Beaconsfield (CA); Denis Labrecque, Laval (CA); Henriette Gourdeau, Montreal (CA)

(73) Assignee: Cytovia, Inc., Tarrytown, NY (US)

( * ) Notice: Subject to any disclaimer, the term of this patent is extended or adjusted under 35 U.S.C. 154(b) by 876 days.

(21) Appl. No.: 11/822,535

(22) Filed: Jul. 6, 2007

(65) Prior Publication Data
US 2008/0085328 A1 Apr. 10, 2008

Related U.S. Application Data

(60) Provisional application No. 60/806,674, filed on Jul. 6, 2006.

(51) Int. Cl.
*A61K 31/353* (2006.01)
*C07D 311/58* (2006.01)
(52) U.S. Cl. .................... 514/456; 549/404
(58) Field of Classification Search ............ 514/456; 549/404
See application file for complete search history.

(56) References Cited

U.S. PATENT DOCUMENTS

| 6,858,607 B1 | 2/2005 | Cai et al. | |
|---|---|---|---|
| 6,906,203 B1 | 6/2005 | Drewe et al. | |
| 7,015,328 B2 | 3/2006 | Cai et al. | |
| 7,053,117 B2 | 5/2006 | Cai et al. | |
| 7,135,480 B2 | 11/2006 | Cai et al. | |
| 7,235,674 B2 | 6/2007 | Cai et al. | |
| 2003/0065018 A1* | 4/2003 | Cai et al. | 514/411 |
| 2005/0154015 A1 | 7/2005 | Drewe et al. | |
| 2005/0165053 A1 | 7/2005 | Cai et al. | |
| 2005/0176750 A1 | 8/2005 | Cai et al. | |
| 2006/0035925 A1 | 2/2006 | Cai et al. | |
| 2006/0104998 A1 | 5/2006 | Cai et al. | |

FOREIGN PATENT DOCUMENTS

| WO | WO 01/34591 A2 | 5/2001 |
|---|---|---|
| WO | WO 02/092076 A1 | 11/2002 |
| WO | WO 02/092594 A1 | 11/2002 |
| WO | WO 2005/046575 A2 | 5/2005 |

OTHER PUBLICATIONS

Miller et al, J. Chromatography A, vol. 865 (1999) pp. 211-226.*
Karrer, Org. Chem. 2nd Ed. (1946), Elsevier Publishing Co., Inc. NY., 1946, pp. 91-102.*

Gourdeau, H., et al., "Antivascular and antitumor evaluation of 2-amino-4-(3-bromo-4, 5-dimethoxy-phenyl)-3-cyano-4H-chromenes, a novel series of anticancer agents," *Molecular Cancer Therapeutics* 3:1375-1383, American Association for Cancer Research (2004).
Kasibhatla, S., et al., "Discovery and mechanism of action of a novel series of apoptosis inducers with potential vascular targeting activity," *Molecular Cancer Therapeutics* 3:1365-1373, American Association for Cancer Research (2004).
Kelland, L.R., Targeting Established Tumor Vasculature: A Novel Approach to Cancer Treatment, *Current Cancer Therapy Reviews* 1:1-9, Bentham Science Publishers Ltd. (2005).
Kemnitzer, W., et al., "Discovery of 4-Aryl-4H-chromenes as a New Series of Apoptosis Inducers Using a Cell- and Caspase-based High-Throughput Screening Assay. 1. Structure-Activity Relationships of the 4-Aryl Group," *J. Med. Chem.* 47:6299-6310, American Chemical Society (2004).
Kemnitzer, W., et al., "Discovery of 4-aryl-4H-chromenes as a new series of apoptosis inducers using a cell- and caspase-besed high-throughput screening assay. 2. Structure-activity relationships of the 7- and 5-, 6-, 8-positions," *Bioorganic & Medicinal Chemistry Letters* 15:4745-4751, Elsevier Science Ltd. (2005).
Kemnitzer, W., et al., "Discovery of 4-Aryl-4H-chromenes as a New Series of Apoptosis Inducers Using a Cell- and Caspase-Based High-Throughput Screening Assay. 3. Structure-Activity Relationships of Fused Rings at the 7,8-Positions," *J. Med. Chem.* 50:2858-2864, American Chemical Society (2007).
Miller, L., et al., "Preparative chromatographic resolution of enantiomers using polar organic solvents with polysaccharide chiral stationary phases," *Journal of Chromatography A* 865:211-226, Elsevier Science Ltd (1999).

(Continued)

*Primary Examiner* — Taofiq A Solola
(74) *Attorney, Agent, or Firm* — Sterne, Kessler, Goldstein & Fox PLLC

(57) ABSTRACT

The present invention is directed to a substituted 4H-chromene represented by the Formula 1R, substantially free from the corresponding (S)-stereoisomer:

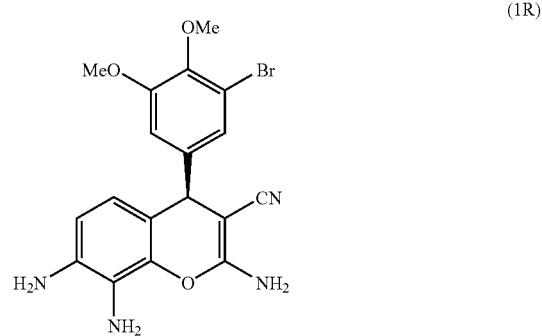

(1R)

The present invention also relates to the discovery that compound 1R, substantially free from the corresponding (S)-stereoisomer, is an activator of caspases and inducer of apoptosis, as well as an antivascular agent. Therefore, compound 1R, substantially free from the corresponding (S)-stereoisomer, can be used to induce cell death in a variety of clinical conditions in which uncontrolled growth and spread of abnormal cells occurs. Compound 1R, substantially free from the corresponding (S)-stereoisomer, also can be used for the treatment of diseases due to overgrowth of vasculature, such as solid tumors and ocular neovascularization.

36 Claims, No Drawings

OTHER PUBLICATIONS

Nambu, H., et al., "Combretastatin A-4 Phosphate Suppresses Development and Induces Regression of Choroidal Neovascularization," *IOVS* 44:3650-3655, Association for Research in Vision and Ophthalmology (2003).

Tozer, G.M., et al., "Disrupting Tumour Blood Vessels," *Nature Reviews Cancer* 5:423-435, Nature Publishing Group (2005).

Vincent, L., et al., "Combretastatin A4 phosphate induces rapid regression of tumor neovessls and growth through interference with vascular endothelial-cadherin signaling," *J. Clin. Invest.* 115:2992-3006, American Society for Clinical Investigation (2005).

Office Action for U.S. Appl. No. 11/150,586, Cai, S.X., filed Jun. 13, 2005, mailed on Jan. 18, 2008.

International Search Report for International Application No. PCT/US07/15676, mailed on Jan. 2, 2008, ISA/US, Virginia, United States of America.

Hutchinson, I., et al., "Antitumor Benzothiazoles. 16.[1] Synthesis and Pharmaceutical Properties of Antitumor 2-(4-Aminophenyl)benzothiazole Amino Acid Prodrugs," *J. Med. Chem.* 45:744-747, American Chemical Society, United States (2002).

Supplementary European Search Report for EP Application No. 07810283.7, Munich, Germany, mailed Aug. 18, 2010 (4 pages).

\* cited by examiner

SUBSTITUTED 4-ARYL-CHROMENE AS ACTIVATOR OF CASPASES AND INDUCER OF APOPTOSIS AND AS ANTIVASCULAR AGENT AND THE USE THEREOF

BACKGROUND OF THE INVENTION

1. Field of the Invention

This invention is in the field of medicinal chemistry. In particular, the invention relates to the discovery that (R)(−)-2,7,8-triamino-4-(3-bromo-4,5-dimethoxyphenyl)-3-cyano-4H-chromene (1R), substantially free from the corresponding (S)-stereoisomer, is an inducer of apoptosis and is a vascular disrupting agent. The invention also relates to the use of compound 1R, substantially free from the corresponding (S)-stereoisomer, as a therapeutically effective anti-cancer agent, and combination with other anticancer agents, as well as for the treatment of diseases due to overgrowth of vasculature, such as ocular neovascularization.

2. Description of Related Art

Organisms eliminate unwanted cells by a process variously known as regulated cell death, programmed cell death, or apoptosis. Such cell death occurs as a normal aspect of animal development, as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237: 529-536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9-34). A cell activates its internally encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529-536 (1995)).

It has been found that a group of proteases is a key element in apoptosis (see, e.g., Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more can be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become immortal—they become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This can be a crucial aspect of the mode of action of most, if not all, known anticancer drugs (Los, et al., Blood 90:3118-3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis occurs, in a phase called M. Antineoplastic drugs, such as cytosine arabinoside, hydroxyurea, 6-mercaptopurine, and methotrexate are S phase specific, whereas antineoplastic drugs, such as vincristine, vinblastine, and paclitaxel are M phase specific. Many slow growing tumors, e.g., colon cancers, exist primarily in the $G_o$ phase, whereas rapidly proliferating normal tissues, e.g., bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225-1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

It is well known that tumor vasculature is essential for the growth and metastasis of solid tumors. Therefore tumor vasculature is an attractive target for therapy because damaging or blocking a single tumor vessel can kill many tumor cells. There are two major therapeutic approaches targeting tumor vasculature. Antiangiogenic approaches, using antiangiogenic agents such as small molecular inhibitors of VEGF receptors or monoclonal antibody targeting VEGF receptors, are designed to prevent the neovascularization processes in tumors, thus blocking the formation of new blood vessels and tumor growth. Antivascular approaches, using vascular disrupting agents (VDAs, which also were known as vascular targeting agents, VTAs), target the preexisting vessels of tumors, causing vascular shutdown and leading to rapid haemorrhagic necrosis and tumor cell death (Tozer, et al., *Nature Review Cancer*, 5:423-435 (2005), and Kelland, *Current Cancer Therapy Reviews*, 1:1-9 (2005)). Vasculature in tumors is known to be proliferating, relatively immature, more permeable and disorganized, in comparison to vasculature in normal tissues. Tumor vascular disrupting agents were designed to exploit these differences between normal and tumor blood vessels and to selectively target tumor vasculature.

Two types of VDAs have been developed. The first types are biological or ligand-directed VDAs which use antibodies, peptides or growth factors to target toxins or pro-coagulants to the tumor endothelium. The second types are small molecule VDAs, and most of them are tubulin-binding agents. Some work through induction of local cytokine production, such as 5,6-dimethylxanthenone-4-acetic acid (DMXAA). VDAs are most effective at killing cells in the poorly perfused hypoxic core of tumors, and leaving a viable rim of well-perfused tumor tissues at the periphery, which can rapidly regrow if not treated. Therefore VDAs as single agents in general have poor anti-tumor effects. However, combination therapies of VDAs with cytotoxic chemotherapy, radiotherapy, and radioimmunotherapy, which target the peripheral tumor cells, have produced excellent responses in many animal tumor models. In general, VDAs are well tolerated and have different side-effect profiles than other types of anticancer therapies. Since VDAs target tumor vasculature, they can kill tumor cells that are resistant to conventional chemotherapy and radiotherapy. In addition, VDAs also should be useful for the treatment of other diseases due to overgrowth of vasculature, such as ocular neovascularization (Numbu, H. et al., *Invest Opthalmol. Vis. Sci.* 44: 3650-5 (2003)).

Vinca alkaloids and colchicine are known to induce haemorrhagic necrosis of solid tumors. However, these antivascular effects were only observed at doses approaching or exceeding their maximum tolerated doses, therefore they could not be used for therapeutic application. More recently, several tubulin-binding agents interacting at the colchicine-binding site have been found to preferentially target tumor endothelial cells while sparing normal vasculature, and to induce haemorrhagic necrosis of solid tumors at doses that are well tolerated. These compounds include combretastatin A-4 phosphate (CA4P), ZD6126 (N-Acetylcolchinol-O-phosphate) and AVE8062, and have shown high antitumor activity in animal studies, especially in combination with other anticancer agents. Therefore vascular disrupting agents (VDAs) are a promising new class of anti-cancer drugs and several VDAs are currently in clinical trials.

In addition, CA4P was reported recently (Vincent, L. et al., *J. Clin. Invest.* 115: 2992-3006 (2005)) to induce rapid regression of tumor neovessels through interference with vascular endothelial-cadherin signaling. Specifically, CA4P was found to selectively target endothelial cells, but not smooth muscle cells, and to induce regression of unstable nascent tumor neovessels by rapidly disrupting the molecular engagement of the endothelial cell-specific junctional molecule vascular endothelial-cadherin both in vitro and in vivo. These results provided a mechanism for the antiangiogenic effects of CA4P and for its selectivity against nascent tumor neovessels as opposed to normal stabilized vasculature. Therefore, VDAs can also have antiangiogenic effects.

EP537949 discloses derivatives of 4H-naphthol[1,2-b]pyran as antiproliferatives:

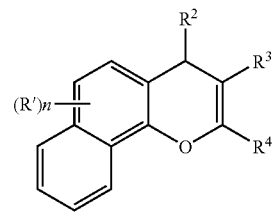

wherein,
each $R^1$ is independently halo, trifluoromethyl, $C_{1-4}$ alkoxy, hydroxy, nitro, $C_{1-4}$ alkyl, $C_{1-4}$ alkylthio, hydroxy-$C_{1-4}$ alkyl, hydroxy-$C_{1-4}$ alkoxy, trifluoromethoxy, carboxy, —$COOR^5$ where $R^5$ is an ester group, —$CONR^6R^7$ or —$NR^6R^7$ where $R^6$ and $R^7$ are each hydrogen or $C_{1-4}$ alkyl;

$R^2$ is phenyl, naphthyl or heteroaryl selected from thienyl, pyridyl, benzothienyl, quinolinyl, benzofuranyl or benzimidazolyl, wherein said phenyl, naphthyl and heteroaryl groups are optionally substituted, or $R^2$ is furanyl optionally substituted with $C_{1-4}$ alkyl;

$R^3$ is nitrile, carboxy, —$COOR^8$ where $R^8$ is an ester group, —$CONR^9R^{10}$ where $R^9$ and $R^{10}$ are each hydrogen or $C_{1-4}$ alkyl or $R^{11}SO_2$ where $R^{11}$ is $C_{1-4}$ alkyl or optionally substituted phenyl;

$R^4$ is —$NR^{12}R^{13}$, —$NHCOR^{12}$, —$N(COR^{12})_2$ or —$N=CHOCH_2R^{12}$ where $R^{12}$ and $R^{13}$ are each hydrogen or $C_{1-4}$ alkyl optionally substituted with carboxy, or $R^4$ is

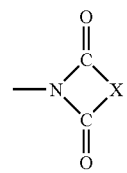

where X is $C_{2-4}$ alkylene, or $R^4$ is —$NHSO_2R^{14}$ where $R^{14}$ is $C_{1-4}$ alkyl or optionally substituted phenyl; and
n is 0-2.

U.S. Pat. No. 5,281,619 discloses naphthopyrans for therapy of diabetic complications:

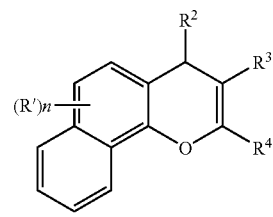

wherein,
$R^1$ is $C_{1-4}$ alkoxy, OH or COOH;
$R^2$ is optionally substituted phenyl;
$R^3$ is nitrile, or $R^3$ is carboxy or —$COOR^8$ when $R^2$ is phenyl substituted with 3-nitro or 3-trifluoromethyl and $R^8$ is an ester group;

$R^4$ is $NR^{12}R^{13}$, —NHCOR$^{12}$, —N(COR$^{12}$)$_2$ or —N=CHOCH$_2R^{12}$, wherein $R^{12}$ and $R^{13}$ are each H or $C_{1-4}$ alkyl; and n is 0-2.

EP599514 discloses the preparation of pyranoquinoline derivatives as inhibitors of cell proliferation:

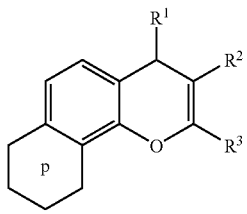

wherein $R^1$ is optionally substituted phenyl or optionally substituted heteroaryl selected from thienyl, pyridyl, benzothienyl, quinolinyl, benzofuranyl or benzimidazolyl, or $R^1$ is furanyl optionally substituted with $C_{1-4}$ alkyl;

$R^2$ is nitrile, carboxy, —CO$_2R^4$ wherein $R^4$ is an ester group, —CON(R$^5$)R$^6$ where $R^5$ and $R^6$ are independently H or $C_{1-4}$ alkyl, or $R^7SO_2$ where $R^7$ is $C_{1-4}$ alkyl or optionally substituted phenyl;

$R^3$ is —NR$^8R^9$, —NHCOR$^8$, —N(CO$_2R^8$)$_2$, —N=CHOR$^8$ where $R^8$ and $R^9$ are independently H or $C_{1-4}$ alkyl, or —NHSO$_2R^{10}$ where $R^{10}$ is $C_{1-4}$ alkyl or optionally substituted phenyl, or

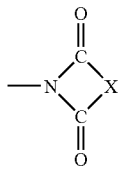

where X is $C_{2-4}$ alkylene; and the ring P represents a pyridine fused to the benzopyran nucleus.

EP618206 discloses the preparation of naphthopyran and pyranoquinoline as immunosuppressants and cell proliferation inhibitors:

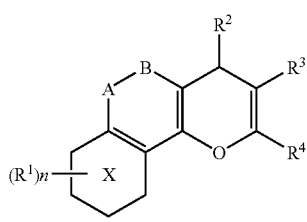

wherein,

A-B is $CH_2CH_2$ or CH=CH;

each $R^1$ is independently halo, carboxy, trifluoromethyl, hydroxy, $C_{1-4}$ alkyl, $C_{1-4}$ alkoxy, $C_{1-4}$ alkylthio, hydroxy-$C_{1-4}$ alkyl, hydroxy-$C_{1-4}$ alkoxy, nitrogen-containing heterocyclyl, nitro, trifluoromethoxy, —COOR$^5$ where $R^5$ is an ester group, —COR$^6$, —CONR$^6R^7$ or —NR$^6R^7$ where $R^6$ and $R^7$ are each hydrogen or $C_{1-4}$ alkyl;

$R^2$ is phenyl, naphthyl or heteroaryl selected from thienyl, pyridyl, benzothienyl, quinolinyl, benzofuranyl or benzimidazolyl, wherein said phenyl, naphthyl and heteroaryl groups are optionally substituted, or $R^2$ is furanyl optionally substituted with $C_{1-4}$ alkyl;

$R^3$ is nitrile, carboxy, —COOR$^8$ where $R^8$ is an ester group, —CONR$^9R^{10}$ where $R^9$ and $R^{10}$ are each hydrogen or $C_{1-4}$ alkyl, or —SO$_2R^{11}$ where $R^{11}$ is $C_{1-4}$ alkyl or optionally substituted phenyl-$C_{1-4}$ alkyl;

$R^4$ is 1-pyrrolyl, 1-imidazolyl or 1-pyrazolyl, each of which is optionally substituted by one or two $C_{1-4}$ alkyl, carboxyl, hydroxyl-$C_{1-4}$ alkyl or —CHO groups, or $R^4$ is 1-(1,2,4-triazolyl), 1-(1,3,4-triazolyl) or 2-(1,2,3-triazolyl), each of which is optionally substituted by a $C_{1-4}$ alkyl or $C_{1-4}$ perfluoroalkyl group, or $R^4$ is 1-tetrazolyl optionally substituted by $C_{1-4}$ alkyl;

X is a pyridine or a benzene ring; and n is 0-2.

EP619314 discloses the preparation of 4-phenyl-4H-naphtho[2,1-b]pyran derivatives:

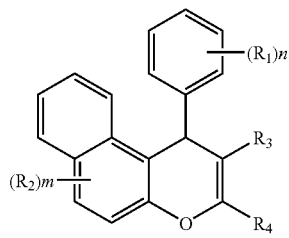

wherein, $R_1$ and $R_2$ are independently halo, trifluoromethyl, $C_1-C_4$ alkoxy, hydroxy, nitro, $C_1-C_4$ alkyl, $C_1-C_4$ alkylthio, hydroxy-$C_1-C_4$ alkyl, hydroxy-$C_1-C_4$ alkoxy, trifluoromethoxy, carboxy, —COOR$_8$ where $R_8$ is an ester group, —COR$_9$, —CONR$_9R_{10}$ or —NR$_9R_{10}$ where $R_9$ and $R_{10}$ are each hydrogen or $C_1-C_4$ alkyl;

$R_3$ is nitrile, carboxy or —CO$_2R_{11}$ wherein $R_{11}$ is an ester group;

$R_4$ is —NR$_{12}R_{13}$, —NR$_{12}$COR$_{13}$, —N(COR$_{12}$)$_2$ or —N=CHOCH$_2R_{12}$ where $R_{12}$ and $R_{13}$ are each hydrogen or $C_{1-4}$ alkyl, or $R_4$ is

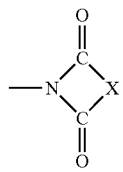

where X is $C_2-C_4$ alkylene, or $R_4$ is optionally substituted 1-pyrrolyl; and m and n are each independently 0-2.

The compounds are said to be useful for the treatment of restenosis, immune disease, and diabetic complications.

Smith, et al., (*Bioorg. Med. Chem. Lett.* 5:2783-2788 (1995)) reported the anti-rheumatic potential of a series of 2,4-di-substituted-4H-naphtho[1,2-b]pyran-3-carbonitriles. They reported that 4-(3-nitrophenyl)-2-(N-succinimido)-4H-naphtho[1,2-b]pyran-3-carbonitrile has proved to be acid stable and still retains biological activity:

Birch, et al., (*Diabetes* 45:642-650 (1996)) reported that LY290181, an inhibitor of diabetes-induced vascular dysfunction, blocks protein kinase C-stimulated transcriptional activation through inhibition of transcription factor binding to a phorbol response element:

LY290181

Panda, et al., (*J. Biol. Chem.* 272: 7681-7687 (1997)) reported the suppression of microtubule dynamics by LY290181, which might be the potential mechanism for its antiproliferative action.

Wood, et al., (*Mol. Pharmacol.* 52: 437-444 (1997)) reported that LY290181 inhibited mitosis and microtubule function through direct tubulin binding.

PCT published patent application WO9824427 disclosed antimicrotubule compositions and methods for treating or preventing inflammatory diseases. LY290181 was listed as an antimicrotubule agent.

PCT published patent application WO01/34591 disclosed 4H-chromenes and analogs as activators of caspases and inducers of apoptosis:

wherein,
X is O, S or $NR_6$, wherein $R_6$ is hydrogen or optionally substituted alkyl;
Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle;
Z is $NR_8R_9$, $NHCOR_8$, $N(COR_8)_2$, $N(COR_8)(COR_9)$, $N=CHOR_8$ or $N=CHR_8$, wherein $R_8$ and $R_9$ are independently H, $C_{1-4}$ alkyl or aryl, or $R_8$ and $R_9$ are combined together with the group attached to them to form a heterocycle;
$R_5$ is hydrogen or $C_{1-10}$ alkyl;
A is optionally substituted and is aryl, heteroaryl, saturated carbocylic, partially saturated carbocylic, saturated heterocyclic, partially saturated heterocyclic, arylalkyl or heteroarylalkyl; and
B is an optionally substituted aromatic or heteroaromatic ring.

PCT published patent application WO02/092076 disclosed substituted coumarins and quinolines and analogs as activators of caspases and inducers of apoptosis:

wherein,
the dashed lines cannot both be a double bond at the same time;
X is O, S or $NR_6$, wherein $R_6$ is hydrogen or optionally substituted alkyl or aryl;
Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle;
Z is O, S, halo, $NR_8$, or $NCOR_8$, wherein $R_8$ is independently H, $C_{1-4}$ alkyl or aryl;
A is optionally substituted and is aryl, heteroaryl, saturated carbocylic, partially saturated carbocylic, saturated heterocyclic, partially saturated heterocyclic, arylalkyl or heteroarylalkyl; and
B is optionally substituted and is an aryl, heteroaryl, saturated carbocyclic, partially saturated carbocyclic, saturated heterocyclic, or partially saturated heterocyclic ring.

PCT published patent application WO02/092083 disclosed 7,8-fused 4H-chromene and analogs as activators of caspases and inducers of apoptosis:

wherein,
X is O, S or $NR_6$, wherein $R_6$ is hydrogen or optionally substituted alkyl;
Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle;

Z is $NR_8R_9$, $NHCOR_8$, $N(COR_8)_2$, $N(COR_8)(COR_9)$, $N=CHOR_8$ or $N=CHR_8$, wherein $R_8$ and $R_9$ are independently H, $C_{1-4}$ alkyl or aryl, or $R_8$ and $R_9$ are combined together with the group attached to them to form a heterocycle;

$R_1$-$R_2$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

$R_5$ is hydrogen or $C_{1-10}$ alkyl;

A is optionally substituted and is aryl, heteroaryl, saturated carbocyclic, partially saturated carbocyclic, saturated heterocyclic, partially saturated heterocyclic, arylalkyl or heteroarylalkyl; and B is optionally substituted and is a fused thiazole, oxazole, 2-imino-imidazole, 2,1,3-thiadiazo-2-one, thiazol-2-one, oxazol-2-one, imidazol-2-thione, thiazol-2-thione, oxazol-2-thione, imidazoline, oxazoline, thiazoline, triazole, oxazine, oxazine-2,3-dione, or piperazine ring.

PCT published patent application WO02/092594 disclosed substituted 4H-chromenes and analogs as activators of caspases and inducers of apoptosis:

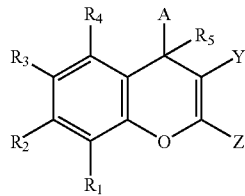

wherein, $R_1R_4$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol; or $R_1$ and $R_2$, or $R_2$ and $R_3$, or $R_3$ and $R_4$, taken together with the atoms to which they are attached form an aryl, heteroaryl, partially saturated carbocyclic or partially saturated heterocyclic group, wherein said group is optionally substituted;

$R_5$ is hydrogen or $C_{1-10}$ alkyl;

A is optionally substituted and is aryl, heteroaryl, saturated carbocyclic, partially saturated carbocyclic, saturated heterocyclic, partially saturated heterocyclic or arylalkyl;

Y is CN, $COR_7$, $CO_2R_7$ or $CONR_xR_y$, wherein $R_7$, $R_x$ and $R_y$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_x$ and $R_y$ are taken together with the nitrogen to which they are attached to form a heterocycle; and Z is $NR_8R_9$, $NHCOR_8$, $N(COR_8)_2$, $N(COR_8)(COR_9)$, $N=CHOR_8$ or $N=CHR_8$, wherein $R_8$ and $R_9$ are independently H, $C_{1-4}$ alkyl or aryl, or $R_8$ and $R_9$ are combined together with the group attached to them to form a heterocycle.

PCT published patent application WO03/097806 disclosed substituted 4-aryl-4H-pyrrolo[2,3-h]chromenes and analogs as activators of caspases and inducers of apoptosis:

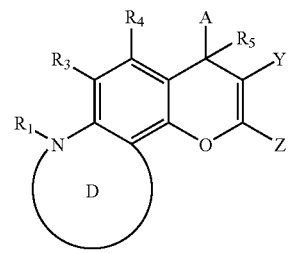

wherein, $R_1$ is selected from the group consisting of alkyl, cycloalkyl, cycloalkylalkyl, hydroxyalkyl, haloalkyl, alkoxyalkyl, aminoalkyl and oxiranylalkyl;

$R_3$ and $R_4$ are independently hydrogen, halo, haloalkyl, aryl, fused aryl, carbocyclic, a heterocyclic group, a heteroaryl group, $C_{1-10}$ alkyl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, nitro, amino, cyano, acylamido, hydroxy, thiol, acyloxy, azido, alkoxy, carboxy, methylenedioxy, carbonylamido or alkylthiol;

$R_5$ is hydrogen or $C_{1-10}$ alkyl;

A is optionally substituted and is aryl, heteroaryl, saturated carbocyclic, partially saturated carbocyclic, saturated heterocyclic, partially saturated heterocyclic or arylalkyl;

D is optionally substituted and is a heteroaromatic, partially saturated heterocyclic or saturated heterocyclic fused ring, wherein said fused ring has 5 or 6 ring atoms, wherein one or two of said ring atoms are nitrogen atoms and the others of said ring atoms are carbon atoms;

Y is CN, $COR_{19}$, $CO_2R_{19}$ or $CONR_{20}R_{21}$, wherein $R_{19}$, $R_{20}$ and $R_{21}$ are independently hydrogen, $C_{1-10}$ alkyl, haloalkyl, aryl, fused aryl, carbocyclic, a heterocyclic group, a heteroaryl group, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl or aminoalkyl; or $R_{20}$ and $R_{21}$ are taken together with the nitrogen to form a heterocycle; and Z is $NR_{22}R_{23}$, $NHCOR_{22}N(COR_{23})_2$, $N(COR_{22})(COR_{23})$, $N=CHOR_{19}$ or $N=CHR_{19}$ wherein $R_{22}$ and $R_{23}$ are independently H, $C_{1-4}$ alkyl or aryl, or $R_{22}$ and $R_{23}$ are combined together with the group attached to them to form a heterocycle.

Kasibhatla, et al., (*Mol. Cancer Ther.* 3:1365-74 (2004)) reported a novel series of 2-amino-4-(3-bromo-4,5-dimethoxy-phenyl)-3-cyano-4H-chromenes as apoptosis-inducing agents discovered using a cell-based apoptosis screening assay. Several analogues from this series including MX-58151, were found to be tubulin destabilizers with binding site at or close to the colchicine binding site. These compounds displayed high selectivity against proliferating versus resting cells, and were shown to disrupt preformed endothelial cell capillary tubules in vitro, suggesting that they should work as tumor vasculature targeting agents.

Gourdean, et al., (*Mol. Cancer. Ther.* 3:1375-84 (2004)) reported the evaluation of a group of 2-amino-4-(3-bromo-4,5-dimethoxy-phenyl)-3-cyano-4H-chromenes to disrupt tumor vasculature and to induce tumor necrosis in vivo. One of the compounds, named MX-116407, was found to be highly active and produced tumor regressions in all testing animals in a human lung tumor xenograft (Calu-6) model. Moreover, MX-116407 significantly enhanced the antitumor activity of cisplatin, resulting in 40% tumor-free animals.

Kemnitzer, et al., (*J. Med. Chem.* 47:6299-310 (2004)) reported the discovery of 4-aryl-4H-chromenes as a new series of apoptosis inducers and the structure-activity relationships (SAR) of the 4-aryl group. 2-Amino-4-(3-bromo-4,5-dimethoxyphenyl)-3-cyano-7-(dimethylamino)-4H-chromene (MX-58151) and 2-amino-3-cyano-7-(dimethylamino)-4-(5-methyl-3-pyridyl)-4H-chromene were identified as the lead compounds from these studies.

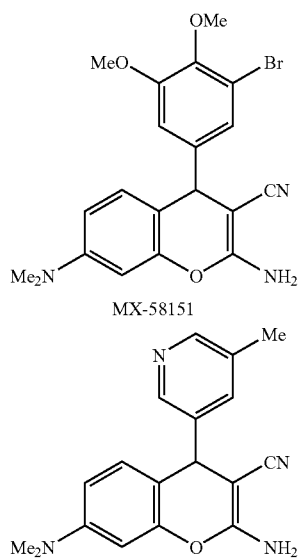

MX-58151

Kemnitzer, et al., (*Bioorg. Med. Chem. Lett.* 15:4745-51 (2005)) reported the exploration of the SAR of 4-aryl-4H-chromenes via modifications at the 7- and 5-, 6-, 8-positions. Several 7-substituted and 7,8-di-substituted compounds, such as 2,7-diamino-4-(3-bromo-4,5-dimethoxyphenyl)-3-cyano-4H-chromene and 2,7,8-triamino-4-(3-bromo-4,5-dimethoxyphenyl)-3-cyano-4H-chromene were found to have similar potencies as MX-58151, both as caspase activators and inhibitors of cell proliferation.

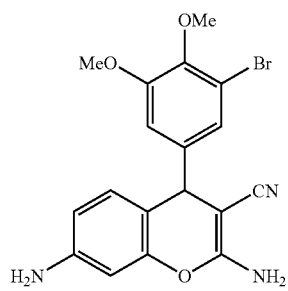

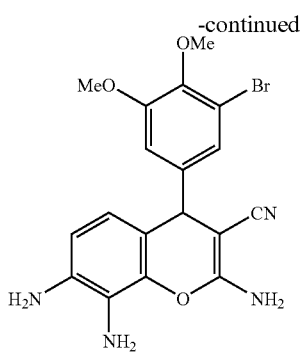

Kemnitzer, et al., (*J. Med. Chem.* 50:2858-2864 (2007)) reported the exploration of the SAR of 4-aryl-4H-chromenes with fused rings at the 7,8-positions. Several of these compounds, such as 2-amino-4-(3-bromo-4,5-dimethoxyphenyl)-3-cyano-4,7-dihydropyrano[2,3-e]indole and 2-amino-4-(3-bromo-4,5-dimethoxyphenyl)-3-cyano-4,9-dihydropyrano[3,2-g]indole were found to be highly active both as caspase activators and inhibitors of cell proliferation.

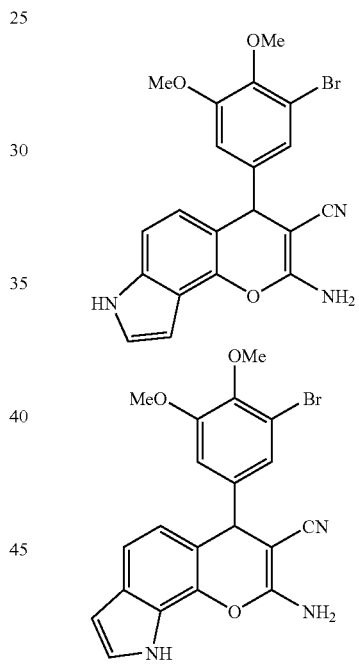

SUMMARY OF THE INVENTION

An embodiment of the present invention relates to the discovery that the R-stereoisomer (1R) of 2,7,8-triamino-4-(3-bromo-4,5-dimethoxyphenyl)-3-cyano-4H-chromene (1) is an activator of the caspase cascade and inducer of apoptosis, and has antivascular effects and is a vascular disrupting agent (VDA) or vascular targeting agent (VTA). Thus, an embodiment of the present invention relates to the use of compound 1R as an inducer of apoptosis and as an antivascular agent.

In another embodiment, the present invention relates to a compound of Formula 1R, substantially free from the corresponding (S)-stereoisomer, or a pharmaceutically acceptable salt or prodrug thereof.

In another embodiment, the present invention relates to a prodrug of 1R having Formula II.

In another embodiment, the present invention relates to a pharmaceutical composition comprising the compound of Formula 1R, or a pharmaceutically acceptable salt or prodrug thereof, and a pharmaceutically acceptable excipient or carrier In another embodiment, the present invention relates to a method of treating a disorder responsive to the induction of apoptosis in an animal suffering therefrom, comprising administering to a mammal in need of such treatment an effective amount of a compound of Formula 1R, substantially free from the corresponding (S)-stereoisomer, or a pharmaceutically acceptable salt or prodrug thereof.

In another embodiment, the present invention relates to a method of treating, preventing or ameliorating neoplasia and cancer by administering compound 1R, substantially free from the corresponding (S)-stereoisomer, to a mammal in need of such treatment.

In another embodiment, the present invention relates to a method of treating a disorder responsive to an antivascular agent in an animal suffering therefrom, comprising administering to a mammal in need of such treatment an effective amount of a compound of Formula 1R, substantially free from the corresponding (S)-stereoisomer, or a pharmaceutically acceptable salt or prodrug thereof.

In another embodiment, the present invention relates to a method for inhibiting the growth of endothelial cells of an animal in need thereof, comprising delivering to the cells a compound of Formula 1R, substantially free from the corresponding (S)-stereoisomer, or a pharmaceutically acceptable salt or prodrug thereof.

In another embodiment, the present invention relates to a method for inhibiting vascularization in a tissue of an animal in need thereof comprising delivering to the tissue a compound of Formula 1R, substantially free from the corresponding (S)-stereoisomer, or a pharmaceutically acceptable salt or prodrug thereof.

In another embodiment, the present invention relates to a method for the separation of an stereoisomer having Formula 1R from the corresponding (S)-stereoisomer, comprising contacting a mixture comprising solvent and a racemic mixture comprising 1R and the corresponding (S)-stereoisomer with a chiral stationary phase, contacting the mixture and the chiral stationary phase with an eluting solvent, and isolating the stereoisomer 1R from the eluting solvent, wherein the stereoisomer 1R is isolated substantially free of the corresponding (S)-stereoisomer.

In another embodiment, the present invention relates to a method of preparing a prodrug of Formula II, comprising contacting a compound of Formula 1R with a protected amino acid and coupling reagent to form a protected prodrug, and deprotecting the protected prodrug to form the compound of Formula II, wherein the compound of Formula 1R is substantially free of the corresponding (S)-stereoisomer.

DETAILED DESCRIPTION OF THE INVENTION

"Substantially free" of a given stereoisomer, refers to the stereoisomeric purity of the stereoisomer, and is used herein to mean there is greater than 95% of the given stereoisomer present. For example, in a given composition of stereoisomer 1R that is substantially free of the corresponding (S)-stereoisomer, 1S, the (R)-stereoisomer is present in greater than 95%. Stereoisomers can be detected using a variety of techniques, for example, chiral HPLC is used.

The present invention arises out of the surprising discovery that when compound 1, 2,7,8-triamino-4-(3-bromo-4,5-dimethoxyphenyl)-3-cyano-4H-chromene, which is a potent and efficacious activator of the caspase cascade and inducer of apoptosis, and exists as a racemic mixture, was separated into the corresponding R-isomer (−) and S-isomer (+), the R-isomer 1R is found to be the active isomer and the S-isomer (+) is found to be essentially inactive. In addition, the R-isomer (−) is found to be an efficacious antivascular agent.

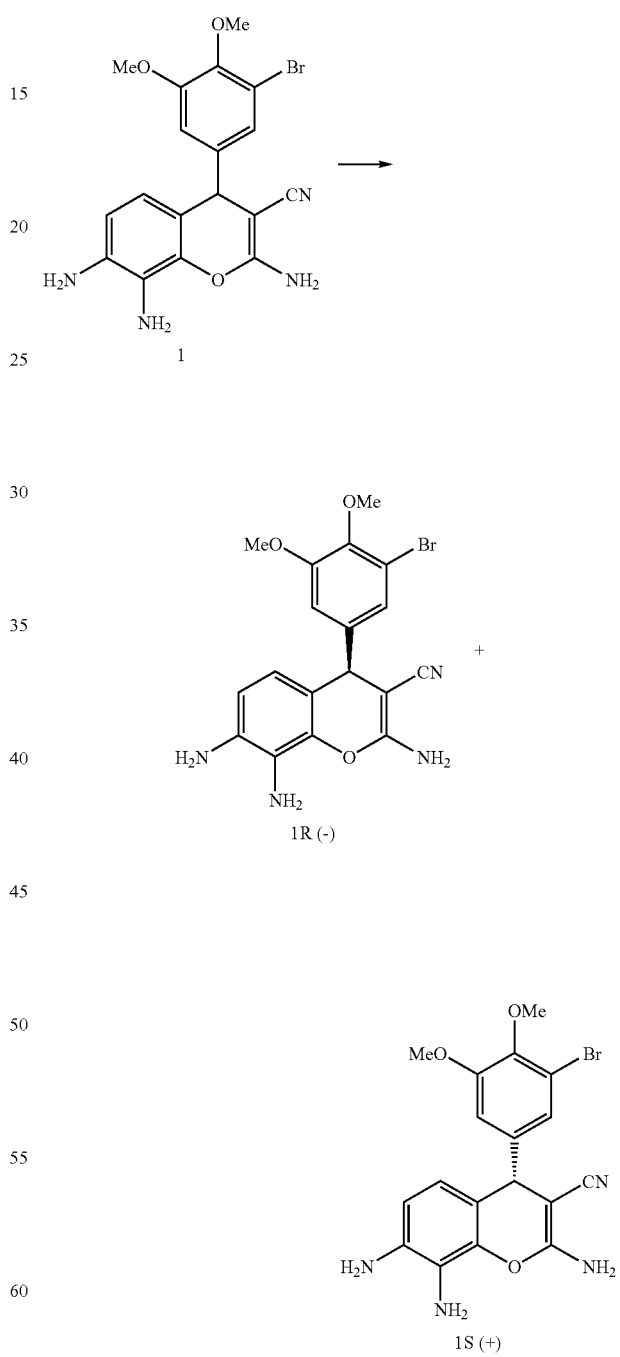

In an embodiment, the present invention relates to a compound of Formula 1R, substantially free from the corresponding (S)-stereoisomer:

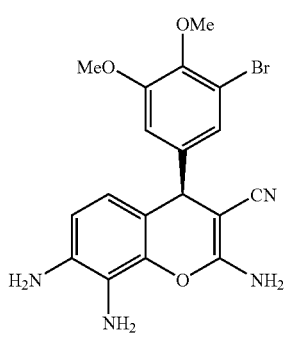

(1R)

or a pharmaceutically acceptable salt or prodrug thereof. In one example, the compound 1R is about 95%, 96%, 97%, 98%, 99% or greater free from the corresponding (S)-stereoisomer. In another example, the compound 1R is about 99.9% free from the corresponding (S)-stereoisomer.

Pharmaceutically acceptable addition salts include, but are not limited to, inorganic and organic acid addition salts, such as hydrochloride, hydrobromide, phosphate, sulphate, citrate, lactate, tartrate, maleate, fumarate, mandelate and oxalate.

Prodrugs for use in the present invention include, but are not limited to, amides (e.g., those obtained by condensation with a $C_{1-40}$ carboxylic acid, such as 4,7,10,13,16,19-docosahexaenoic acid (DHA), $C_{3-6}$ dioic acid or anhydride thereof, such as succinic and fumaric anhydrides, amino acids, such as glycine or alanine, according to methods known in the art); imines (e.g., those obtained by condensation with a $C_{1-4}$ aldehyde or ketone according to methods known in the art); and carbamate, such as those described by Leu, et. al., (J. Med. Chem. 42:3623-3628 (1999)) and Greenwald, et. al., (J. Med. Chem. 42:3657-3667 (1999)).

Amino acids for use in the present invention include natural and non-natural amino acids. Natural amino acids for use in the present invention include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

One specific group of prodrugs are amides prepared using amino acid, especially natural amino acid. Specifically, prodrug of compound 1R having the Formula of II:

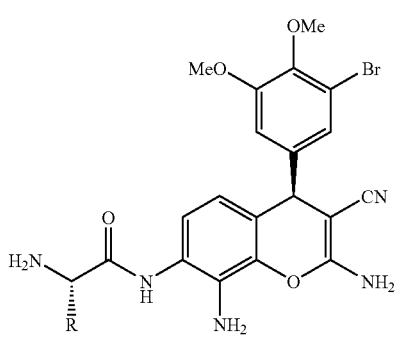

(II)

or a pharmaceutically acceptable salt or prodrug thereof, wherein

R is hydrogen, alkyl and alkyl substituted with hydroxy, carboxy, carbamoyl, mercapto, imidazolyl, methylthio, aryl, amino or guanidine, or R and the $NH_2$ group that is bonded to the carbon atom to which R is bonded, are taken together to form a ring such as in proline.

Compound 1 can be prepared using any method known in the art. In one example, compound 1 is prepared as illustrated in Scheme 1. Reaction of 2,3-diaminophenol with 5-bromoveratraldehyde (3-bromo-4,5-dimethoxybenzaldehyde) and malononitrile in the presence of a base such as dimethylisopropylamine (DMIPA) in a solvent such as ethanol produced the racemic mixture 1 in yield of 82-90%.

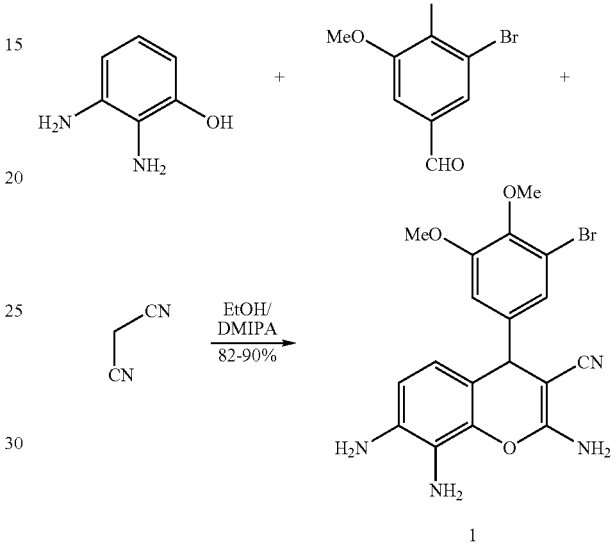

In another embodiment, as shown in Scheme 2, the present invention relates to a method for the separation of stereoisomers having Formula 1R or 1S from their racemic mixture having Formula 1. In one example, the stereoisomer 1R or 1S can be isolated from the eluting solvent substantially free from the other corresponding stereoisomer. In another example, the stereoisomer 1R can be isolated from the eluting solvent about 96, 97, 98, 99% or greater free from the other corresponding stereoisomer. In another example, the stereoisomer 1R can be isolated from the eluting solvent about 99% free from the other corresponding stereoisomer. In another example, the stereoisomer 1R can be isolated from the eluting solvent about 99.9% free from the other corresponding stereoisomer.

In another embodiment, as shown in Scheme 2, the present invention relates to a method for the separation of a stereoisomer having Formula 1R from the corresponding (S)-stereoisomer. The method includes contacting a mixture comprising solvent and a racemic mixture comprising 1R and the corresponding (S)-stereoisomer with a chiral stationary phase, contacting the mixture and the chiral stationary phase with an eluting solvent, and isolating said stereoisomer 1R from the eluting solvent, wherein the stereoisomer 1R is isolated substantially free of the corresponding (S)-stereoisomer. In another example, the stereoisomer 1R is isolated about 99% free from the corresponding (S)-stereoisomer.

The phrase "chiral stationary phase" refers to separation media capable of separating corresponding stereoisomers (enantiomeric compounds). The chiral stationary phase can include chiral molecules and/or polymers bonded to solid supports, chiral phases created in situ on the surface of the solid adsorbent, or surface cavities that allow for specific interactions with one stereoisomer. For example, chiral stationary phases for use in the present invention include, but are not limited to, stationary phases in which chiral proteins, small chiral molecules, polymers of cellulose or amylose, marocyclic glycopeptides or cyclodextrins are coated, bonded or otherwise adsorbed to silica or other solid matrices. Another example of a chiral stationary phase for use in the present invention is an Amylose tris[(S)-α-methylbenzylcarbamate] coated on 20 μm silica gel (available from Daicel Chemical Industries, Ltd. as the CHIRALPAK® AS-V, Tokyo, Japan).

Example solvents for use in the chiral separation include MeOH and acetonitrile. Other solvents can be used, for example, ethyl acetate and ethanol.

In other embodiments, the racemic mixture 1 can also be separated using other methods, including supercritical fluid conditions (SFC) or using simulated moving bed (SMB) technology.

A simulated moving bed apparatus which allows for the separation of 1R from a mixture of 1R and 1S is commercially available from, for example, NovaSep, Inc., Boothwyn, Pa., or from Knauer, ASI, Franklin, Mass. (CSEP® Models). See, for example, the apparatuses disclosed in U.S. Pat. Nos. 3,268,605; 4,434,051 and 5,456,825. See also U.S. Pat. Nos. 5,126,055; 5,434,298 and 6,533,936 for methods of purifying stereoisomers using simulated moving bed technology.

Scheme 2

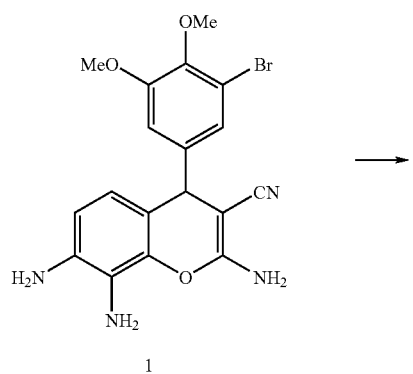

1

+

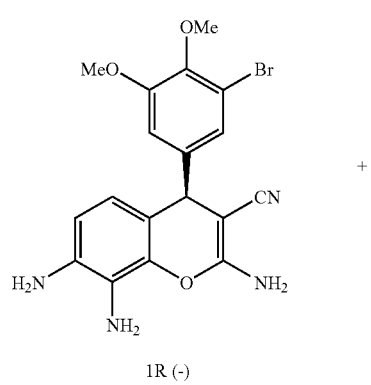

1R (−)

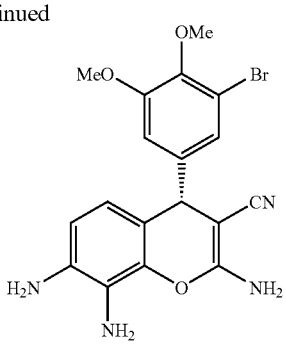

1S (+)

Another embodiment of the present invention relates to a method of producing a prodrug of Formula II. The method includes contacting a compound of Formula 1R with a protected amino acid and coupling reagent to form a protected prodrug, and deprotecting the protected prodrug to form the compound of Formula II. The compound of Formula 1R is substantially free of the corresponding (S)-stereoisomer.

Protected amino acids for use in the present invention include protected natural and non-natural amino acids. In one example, the protected amino acid is 9-fluorenylmethyl carbamate protected L-alanine (Fmoc-L-alanine).

Coupling reagents for use in the present invention include those reagents that efficiently, and in high yield, couple amino acids to amino groups. For example, the coupling reagent is a mixture that includes dicyclohexylcarbodiimide (DCC) and hydroxybenzotriazole (HOBt), or in another example, the coupling reagent is a mixture that includes 1-ethyl-3-(3-dimethylaminopropyl)-carbodiimide (EDC) and hydroxybenzotriazole (HOBt). It is understood by one ordinary skill in the art that other coupling reagents can be used.

Protected prodrugs can be deprotected using any method that efficiently, and in high yield, cleaves the protecting group from the prodrug. For example, the protected prodrug is deprotected using aqueous base. Examples of base for use in the deprotection includes, but are not limited to, aqueous hydroxide bases, including aqueous solutions of a hydroxide salt. Hydroxide salts include, for example, ammonium, sodium, calcium potassium and magnesium hydroxide.

In one embodiment, amino acid prodrugs of compound 1R can be prepared as shown in Scheme 3. Reaction of 1R with a 9-fluorenylmethyl carbamate (Fmoc) protected amino acid, such as Fmoc-L-alanine, in the presence of coupling agents, such as dicyclohexylcarbodiimide (DCC) and hydroxybenzotriazole (HOBt), produced the protected prodrug, Fmoc-alanine amide, of 1R. The Fmoc protecting group can be removed under basic conditions, such as using 2N NaOH, to produce the alanine amide of 1R, which is expected to have better aqueous solubility than that of 1R due to the presence of the more basic amino group. When the amide prodrug is injected into animals, such as mice or human, it is expected that the amino acid will be removed by amino peptidase to produce the active drug 1R.

Scheme 3

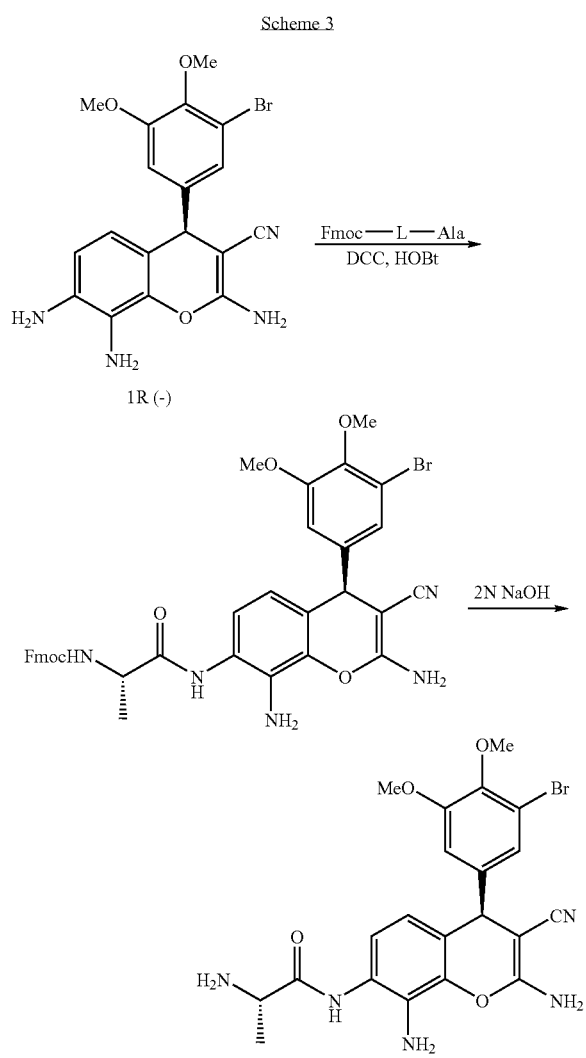

An embodiment of the present invention relates to the discovery that compound 1R is an activator of caspases and inducer of apoptosis. Therefore, compound 1R is useful in a variety of clinical conditions in which there is uncontrolled cell growth and spread of abnormal cells, such as in the case of cancer.

Another embodiment of the present invention relates to the discovery that compound 1R is a potent and highly efficacious activator of caspases and inducer of apoptosis in drug resistant cancer cells, such as breast and prostate cancer cells, which enables it to kill these drug resistant cancer cells. In comparison, most standard anti-cancer drugs are not effective in killing drug resistant cancer cells under the same conditions. Therefore, compound 1R is useful for the treatment of drug resistant cancer in animals.

Another embodiment of the present invention relates to the discovery that compound 1R is a potent antivascular agent. Therefore, compound 1R is useful for inhibiting the growth of endothelial cells and inhibiting the vascularization of a tissue. In particular, compound 1R is useful for the treatment of cancer in animals via targeting or disrupting vasculature in tumors, blocking blood supply to the tumors and causing tumor cell death. Compound 1R also is expected to be useful for the treatment of other diseases due to overgrowth of vasculature, such as ocular neovascularization.

Another embodiment of the present invention relates to a therapeutic method useful to modulate in vivo apoptosis or in vivo neoplastic disease, comprising administering to a subject in need of such treatment an effective amount of compound 1R, substantially free from the corresponding (S)-stereoisomer, or a pharmaceutically acceptable salt or prodrug, which functions as a caspase cascade activator and inducer of apoptosis.

Another embodiment of the present invention relates to a therapeutic method comprising administering to an animal an effective amount of compound 1R, substantially free from the corresponding (S)-stereoisomer, or a pharmaceutically acceptable salt or prodrug of said compound, wherein said therapeutic method is useful to treat cancer, which is a group of diseases characterized by the uncontrolled growth and spread of abnormal cells. Such diseases include, but are not limited to, Hodgkin's disease, non-Hodgkin's lymphoma, acute lymphotic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinomas, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods of the present invention, effective amounts of compositions containing therapeutically effective concentrations of the compound formulated for oral, intravenous, local and topical application, for the treatment of cancer, neoplastic diseases and other diseases in which caspase cascade mediated physiological responses are implicated, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount can be administered as a single dosage or can be administered according to a regimen, whereby it is effective. The amount can cure the disease but, typically, is administered in order to ameliorate the disease. Typically, repeated administration is required to achieve the desired amelioration of symptoms.

Another embodiment of the present invention relates to a pharmaceutical composition comprising compound 1R, or a pharmaceutically acceptable salt or prodrug of said compound, which functions as a caspase cascade activator and inducer of apoptosis in combination with a pharmaceutically acceptable vehicle is provided. In one example, the pharmaceutical composition comprising compound 1R is substantially free of the corresponding (S)-stereoisomer. In another example, the pharmaceutical composition comprising compound 1R is about 95, 96, 97, 98 or 99% or greater free of the corresponding (S)-stereoisomer. In another example, the pharmaceutical composition comprising compound 1R is about 99.9% free from the corresponding (S)-stereoisomer.

Another embodiment of the present invention relates to a composition effective to treat cancer comprising compound 1R, or a pharmaceutically acceptable salt or prodrug of said compound, which functions as a caspase cascade activator and inducer of apoptosis, in combination with at least one known cancer chemotherapeutic agent, or a pharmaceutically acceptable salt of said agent. Examples of known anti-cancer agents which can be used for combination therapy include, but not are limit to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents which can be used for combination therapy include melphalan, chlorambucil, cyclophosphamide, ifosfamide, vincristine, mitoguazone, epirubicin, aclarubicin, bleomycin, mitoxantrone, elliptinium, fludarabine, octreotide, retinoic acid, tamoxifen and alanosine.

Another embodiment of the present invention relates to a composition effective to treat cancer comprising compound 1R, or a pharmaceutically acceptable salt or prodrug of said compound, which functions as a caspase cascade activator, inducer of apoptosis, and as a vascular disrupting agent, in combination with at least one approved cancer therapeutic agent (approved now or in the future), or a pharmaceutically acceptable salt of said agent. These combinations of compound 1R with approved cancer therapeutic agents include, as examples, combination with sunitinib, e.g. for the treatment of renal cell cancer; combination with sorafenib, e.g. for the treatment of liver cancer; combination with carbotaxel or bevacuzimab, e.g. for the treatment of non-small cell lung cancer; combination with doxorubicin, e.g. for the treatment of ovarian cancer; combination with satraplatin, e.g. for the treatment of prostate cancer; and combination with bevacuzimab, e.g. for the treatment of colorectal cancer. The approved cancer therapeutic can be used at its approved dose and schedule, such as once every 21 days. Compound 1R can be administered, for example, starting the day before, the same day or the day after the approved therapeutic agent. Compound 1R can be administered once a day for 3 consecutive days on a 21 days cycle. Alternative cycles for compound 1R can be, as an example, once a week for 3 weeks on a 28 days cycle. These combination treatments are expected to provide a statistically significant improvement in the reduction of disease progression compared to when the approved cancer therapeutic agent is administered alone.

In practicing the methods of the present invention, the compound of the invention can be administered together with at least one known chemotherapeutic agent as part of a unitary pharmaceutical composition. Alternatively, the compound of the invention can be administered apart from the at least one known cancer chemotherapeutic agent. In one embodiment, the compound of the invention and the at least one known cancer chemotherapeutic agent are administered substantially simultaneously, i.e. the compounds are administered at the same time or one after the other, so long as the compounds reach therapeutic levels in the blood at the same time. In another embodiment, the compound of the invention and the at least one known cancer chemotherapeutic agent are administered according to their individual dose schedule, so long as the compounds reach therapeutic levels in the blood.

Another embodiment of the present invention relates to a composition effective to treat cancer comprising a bioconjugate of said compound 1R, which functions as a caspase cascade activator and inducer of apoptosis, in bioconjugation with at least one known therapeutically useful antibodies, such as Herceptin® or Rituxan®, growth factors such as DGF, NGF, cytokines, such as IL-2, IL-4, or any molecule that binds to cell surface. The antibodies and other molecules will deliver compound 1R to its targets and make it an effective anticancer agent. The bioconjugates also could enhance the anticancer effect of therapeutically useful antibodies, such as Herceptin® or Rituxan®.

Another embodiment of the present invention relates to a composition effective to treat cancer comprising compound 1R or a pharmaceutically acceptable salt or prodrug of said compound, which functions as a caspase cascade activator and inducer of apoptosis, in combination with radiation therapy. In this embodiment, the compound of the invention can be administered at the same time as the radiation therapy is administered or at a different time.

Another embodiment of the present invention relates to a composition effective for post-surgical treatment of cancer, comprising compound 1R, or a pharmaceutically acceptable salt or prodrug of said compound, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms maintaining immune homeostasis. This deletion of reactive cells has been shown to be regulated by a phenomenon known as apoptosis. Autoimmune diseases have been identified as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly and generalized lymphadenopathy, hypergammaglobulinemia, and autoantibody formation. (Infante, A. J., et al., *J. Pediatr.* 133:629-633 (1998) and Vaishnaw, A. K., et al., *J. Clin. Invest.* 103:355-363 (1999)). It was reported that overexpression of Bcl-2, which is a member of the Bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1:475-483 (1998)). It is therefore evident that many types of autoimmune disease are caused by defects of the apoptotic process, and one treatment strategy would be to turn on apoptosis in the lymphocytes that are causing autoimmune disease (O'Reilly, L. A. & Strasser, A., *Inflamm. Res.* 48:5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603-608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes can have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells, both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou, T., et al., (*Nat. Med.* 5:42-48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, can be therapeutically useful for the more effective elimination of detrimental cells and inhibition of T cell-mediated autoimmune diseases. Therefore, an effective amount of compound 1R, or a pharmaceutically acceptable salt or prodrug of compound 1R, which functions as a caspase cascade activator and inducer of apoptosis, is an effective treatment for autoimmune disease.

Psoriasis is a chronic skin disease that is characterized by scaly red patches. Psoralen plus ultraviolet A (PUVA) is a widely used and effective treatment for psoriasis vulgaris and Coven, et al. (*Photodermatol. Photoimmunol. Photomed.* 15:22-27 (1999)) reported that lymphocytes treated with psoralen 8-MOP or TMP plus UVA displayed DNA degradation patterns typical of apoptotic cell death. Ozawa, et al. (*J. Exp. Med.* 189:711-718 (1999)) reported that induction of T cell apoptosis could be the main mechanism by which 312-nm UVB resolves psoriasis skin lesions. Low doses of methotrexate can be used to treat psoriasis to restore a clinically normal skin. Heenen, et al. (*Arch. Dermatol. Res.* 290:240-245 (1998)) reported that low doses of methotrexate can induce apoptosis and this mode of action could explain the reduction in epidermal hyperplasia during treatment of psoriasis with methotrexate. Therefore, an effective amount of compound 1R, or a pharmaceutically acceptable salt or prodrug of compound 1R, which functions as a caspase cascade activator and inducer of apoptosis, is an effective treatment for hyperproliferative diseases, such as psoriasis.

Synovial cell hyperplasia is a characteristic of patients with rheumatoid arthritis (RA). Excessive proliferation of RA synovial cells, as well as those defective in synovial cell death, might be responsible for the synovial cell hyperplasia. Wakisaka, et al. (*Clin. Exp. Immunol.* 114:119-128 (1998)) found that although RA synovial cells could die via apoptosis through Fas/FasL pathway, apoptosis of synovial cells was inhibited by proinflammatory cytokines present within the synovium, and suggested that inhibition of apoptosis by the proinflammatory cytokines can contribute to the outgrowth of synovial cells, and lead to pannus formation and the destruction of joints in patients with RA. Therefore, an effective amount of compound 1R, or a pharmaceutically acceptable salt or prodrug of compound 1R, which functions as a caspase cascade activator and inducer of apoptosis, is an effective treatment for rheumatoid arthritis.

Convincing evidence has been accumulating that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375-380 (1997)). Boirivant, et al. (*Gastroenterology* 116:557-565 (1999)) reported that lamina propria T cells isolated from areas of inflammation in Crohn's disease, ulcerative colitis, and other inflammatory states manifest decreased CD2 pathway-induced apoptosis, and that studies of cells from inflamed Crohn's disease tissue indicate that this defect is accompanied by elevated Bcl-2 levels. Therefore, an effective amount of compound 1R, or a pharmaceutically acceptable salt or prodrug, which functions as a caspase cascade activator and inducer of apoptosis, is an effective treatment for inflammation and inflammatory bowel disease.

Compositions within the scope of the present invention include all compositions wherein compound 1R is contained in an amount that is effective to achieve its intended purpose. While individual needs vary, determination of optimal ranges of effective amounts of each component is within the skill of the art. Typically, the compounds can be administered to mammals, e.g., humans, orally at a dose of 0.0025 to 50 mg/kg, or an equivalent amount of the pharmaceutically acceptable salt thereof, per day, of the body weight of the mammal being treated for apoptosis-mediated disorders. In one example, about 0.01 to about 10 mg/kg is orally administered to treat or prevent such disorders. For intramuscular injection, the dose is generally about one-half of the oral dose. For example, a suitable intramuscular dose would be about 0.0025 to about 25 mg/kg, and another example would be from about 0.01 to about 5 mg/kg. If a known cancer chemotherapeutic agent is also administered, it is administered in an amount which is effective to achieve its intended purpose. The amounts of such known cancer chemotherapeutic agents effective for cancer are well known to those of skill in the art.

In one example, the unit oral dose comprises about 0.01 to about 50 mg. In another example, the unit oral dose comprises about 0.1 to about 10 mg of the compounds of the present invention. The unit dose can be administered one or more times daily as one or more tablets, each containing from about 0.1 to about 10, conveniently about 0.25 to 50 mg of the compound or its solvates.

In a topical formulation, the compound can be present at a concentration of about 0.01 to 100 mg per gram of carrier.

In addition to administering the compound as a raw chemical, the compounds of the present invention can be administered as part of a pharmaceutical preparation. The pharmaceutical preparation can contain suitable pharmaceutically acceptable carriers that include, for example, excipients and auxiliaries. The excipients and auxiliaries facilitate processing the compounds into preparations which can be used pharmaceutically.

In one example, the orally administered preparations comprise 0.01 to 99 percent, of active compound(s), together with the excipient. In another example, the orally administered preparations comprise about 0.25 to 75 percent of active compound(s), together with the excipient. In further exemplary embodiments, tablets, dragees, or capsules can be used as the forms for orally administering the compounds of the present invention.

In another example, the rectally administered preparations, as well as oral solutions and solutions for injection, comprise about 0.01 to 99 percent of active compound(s), together with the excipient. In another example, these preparations comprise from about 0.25 to 75 percent of active compound(s), together with the excipient. In a further example, suppositories can be used as the form for rectally administering the compounds of the present invention.

The pharmaceutical compositions of the invention can be administered to any animal that can experience the beneficial effects of the compounds of the invention. Foremost among such animals are mammals, e.g., humans and veterinary animals, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, intrathecal, intracranial, intranasal or topical; routes. Alternatively, or concurrently, administration can be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, e.g., by means of conventional mixing, granulating, dragee-making, dissolving, or lyophilizing processes. Thus, pharmaceutical preparations for oral use can be obtained by combining the active compounds with solid excipients, optionally grinding the resultant mixture and processing the mixture of granules, after adding suitable auxiliaries, if desired or necessary, to obtain tablets or dragee cores.

Excipients for use in the present invention include, but are not limited to, fillers, such as saccharides, e.g., lactose or sucrose, mannitol or sorbitol; cellulose preparations and/or calcium phosphates, e.g., tricalcium phosphate or calcium hydrogen phosphate; and binders, such as starch paste, using, e.g., maize starch, wheat starch, rice starch, potato starch, gelatin, tragacanth, methyl cellulose, hydroxypropylmethyl-cellulose, sodium carboxymethylcellulose, and/or polyvinyl pyrrolidone. Optional, disintegrating agents can be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, optionally, are resistant to gastric juices. For this purpose, concentrated saccharide solutions can be used, which can optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments can be added to the tablets or dragee coatings, e.g., for identification or in order to characterize combinations of active compound doses.

Other pharmaceutical preparations, which can be used orally, include push-fit capsules made of gelatin, as well as soft, sealed capsules made of gelatin and a plasticizer, such as glycerol or sorbitol. The push-fit capsules can contain the active compounds in the form of granules, which can be mixed with fillers, such as lactose, binders such as starches, and/or lubricants such as talc or magnesium stearate and, optionally, stabilizers. In soft capsules, the active compounds are dissolved or suspended in suitable liquids, such as fatty oils, or liquid paraffin. Stabilizers can optionally be added.

Pharmaceutical preparations which can be used rectally include, e.g., suppositories, which consist of a combination of one or more of the active compounds with a suppository base. For example, suitable suppository bases are natural or synthetic triglycerides, or paraffin hydrocarbons. In addition, it is also possible to use gelatin rectal capsules, which consist of a combination of the active compounds with a base. Possible base materials include, e.g., liquid triglycerides, polyethylene glycols, or paraffin hydrocarbons.

Formulations for parenteral administration include aqueous solutions of the active compounds in water-soluble form, e.g., water-soluble salts and alkaline solutions. The active compound can be present in about 0.01 to about 50 mg/mL. In addition, suspensions of the active compounds as appropriate oily injection suspensions can be administered.

Suitable lipophilic solvents, vehicles, excipients or carriers include fatty oils, e.g., sesame oil, or synthetic fatty acid esters, e.g., ethyl oleate or triglycerides; polyethylene glycols ("PEG"), e.g., PEG-200, 400, 600, 800 or 1000; cremophor; cyclodextrins; or block copolymers of poly(ethylene glycol) and poly(propylene glycol) ("poloxamers"), e.g., LUTROL®. In one example, the excipient or carrier is selected from the group consisting of poly(ethylene glycol), block copolymers of poly(ethylene glycol) and poly(propylene glycol), and saline. In another example, a pharmaceutical composition for use in the present invention includes about 10 mg/mL of the compound 1R, substantially free from the corresponding (S)-stereoisomer, about 25% (v/v) poly(ethylene glycol), about 5% (v/v) block copolymers of poly(ethylene glycol) and poly(propylene glycol) and saline.

Aqueous injection suspensions can contain substances, which increase the viscosity of the suspension, e.g., sodium carboxymethyl cellulose, sorbitol, polysorbate, e.g. polysorbate 20, 80, 81, 90 and 94 (e.g., TWEEN®), dextrose, e.g. 1%, 2%, 5%, 10% or 20% solutions of dextrose in water (e.g., 5% dextrose in water "D5W"), and/or dextran. Optionally, the suspension can also contain stabilizers. In one example, the excipient or carrier is selected from the group consisting of poly(ethylene glycol), polysorbate, and a solution of 5% dextrose in water. In another example, a pharmaceutical composition for use in the present invention includes about 10 mg/mL of the compound 1R, substantially free from the corresponding (S)-stereoisomer, about 7% (v/v) poly(ethylene glycol) 400, about 9% (v/v) polysorbate 80 and about 84% (v/v) of a solution of 5% dextrose in water.

In accordance with an embodiment of the present invention, compounds of the invention are employed in topical and parenteral formulations and are used for the treatment of skin cancer.

The topical compositions of this invention are formulated as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). Particular examples of carriers include those in which the active ingredient is soluble. Emulsifiers, stabilizers, humectants and antioxidants can also be included, as well as agents imparting color or fragrance, if desired. Additionally, transdermal penetration enhancers can be employed in these topical formulations. Examples of such enhancers can be found in U.S. Pat. Nos. 3,989,816 and 4,444,762.

In on example, creams are formulated from a mixture of mineral oil, self-emulsifying beeswax and water, in which the active ingredient, dissolved in a small amount of an oil, such as almond oil, is admixed. A typical example of such a cream is one which includes about 40 parts water, about 20 parts beeswax, about 40 parts mineral oil and about 1 part almond oil.

Ointments can be formulated by mixing a solution of the active ingredient in a vegetable oil, such as almond oil with warm soft paraffin, and allowing the mixture to cool. A typical example of such an ointment is one which includes about 30% almond oil and about 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

Synthesis of 2,7,8-Triamino-4-(3-bromo-4,5-dimethoxy-phenyl)-3-cyano-4H-chromene (1)

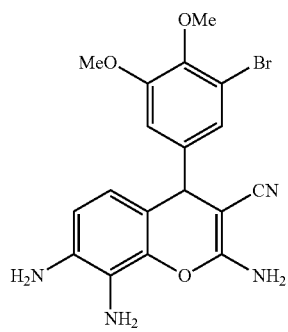

1

A suspension of 3-bromo-4,5-dimethoxybenzaldehyde (1500 g, 6.12 moles, 1.1 eq) and malononitrile (404 g, 6.12 moles, 1.1 eq) in ethanol 99% (12 L, 7 volumes) was stirred at room temperature under $N_2(g)$. Dimethylisopropylamine (339 mL, 2.78 moles, 0.5 eq) was added slowly (which caused an exotherm from about 14° C. to about 26° C.) and the reaction mixture was stirred at room temperature for about 2 h under $N_2(g)$. The yellow thick suspension was analyzed by HPLC to monitor the appearance of the Knoevenagel intermediate and the disappearance of the aldehyde. 2,3-Diaminophenol (690.66 g, 5.56 moles, 1 eq) was added and the reaction mixture was stirred at room temperature overnight. The resulting beige-brown suspension was filtered and the cake was washed with cold $CH_2Cl_2$ (3000 mL). The solids were dried under vacuum to give 2,7,8-triamino-4-(3-bromo-4,5-dimethoxy-phenyl)-3-cyano-4H-chromene (1.9 kg, 82% yield). $^1$H NMR (300 MHz) (DMSO-$d_6$, ppm): 3.71 (s, 3H), 3.82 (s, 3H), 4.43 (s, 2H), 4.56 (s, 1H), 4.70 (s, 2H), 6.09 (d, J=8 Hz, 1H), 6.26 (d, J=8 Hz, 1H), 6.76 (s, 2H), 6.78 (d, J=2 Hz, 1H), 6.90 (d, J=2 Hz, 1H).

EXAMPLE 2

Separation of 2,7,8-Triamino-4-(3-bromo-4,5-dimethoxy-phenyl)-3-cyano-4H-chromene (1) to Produce R(−)-2,7,8-triamino-4-(3-bromo-4,5-dimethoxy-phenyl)-3-cyano-4H-chromene (1R) by Chiral Preparative HPLC

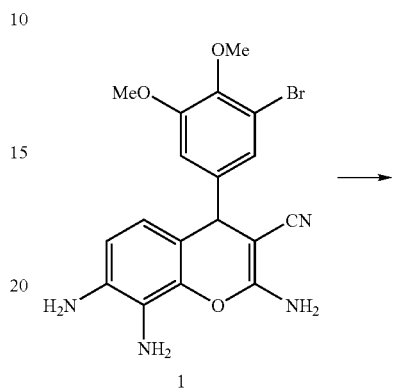

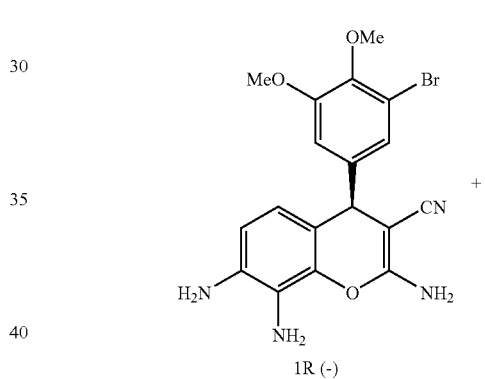

1R (−)

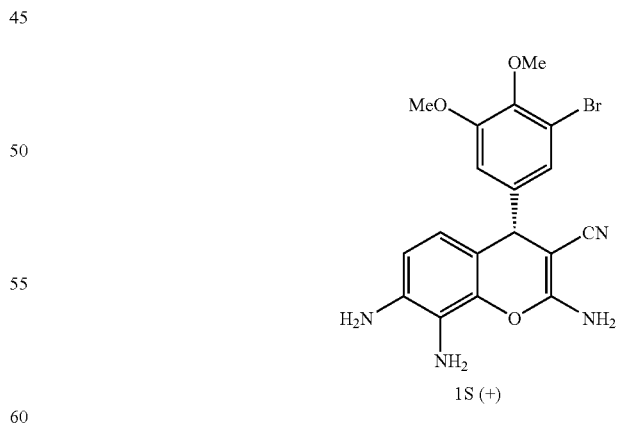

1S (+)

A solution of 2,7,8-triamino-4-(3-bromo-4,5-dimethoxy-phenyl)-3-cyano-4H-chromene (1) in MeOH/CH$_3$CN: 95/5 was prepared for injection into a LC110 (internal diameter 110 mm) column packed with CHIRALPAK® AS-V 20 μM silica gel, using a solution of MeOH/CH$_3$CN: 95/5 as eluent, under the following general conditions:

General Conditions

| Parameters | Set up |
| --- | --- |
| Temperature of the eluent | 30° C. |
| Temperature of the column | 30° C. |
| Flow of the eluent | About 570 mL/min |
| Flow of feed | About 570 mL/min |
| Quantity of feed | 230 mL |
| Feed concentration | 5.5 g/L |
| Cycle time | About 4.25 min |
| Elution sequence | Isocratic |
| Fractions | F1 (S-isomer) |
|  | F2 (R-isomer) |

The fractions were collected and combined separately to give compound 1R and 1S. The compounds were analyzed using CHIRALPAK® AS-H 5 μm (150×4.6 mm) analytical column under the following HPLC parameters:

| Parameter | Condition |
| --- | --- |
| Mobile Phase A | Methanol |
| Flow rate | 0.7 mL/min |
| Detection wavelength | 254 nm |
| Column temperature | 30° C. |
| Autosampler temperature | 5° C. |
| Run time | 6 min |
| Data collection time | 6 min |
| Injection volume | 5 μL |

Compound 1R and compound 1S were found to have a retention time of 3.19 min and 4.12 min, respectively under these conditions. In addition, compound 1R and compound 1S were found to have optical rotation value $\alpha_D = -38.46°$ and $\alpha_D = +44.62°$ at 25° C. in MeOH, respectively. The absolute configuration of compound 1R was determined by single crystal structure analysis.

HPLC analysis of the racemic mixture 1 showed both stereoisomers were present in about equal proportions. After performing the separation, further HPLC analysis of the isolated stereoisomer 1R showed that it was about 99.9% free of the corresponding (S)-stereoisomer.

EXAMPLE 3

Synthesis of (9H-fluoren-9-yl)methyl(S)-1-((R)-2,8-diamino-3-cyano-4-(3-bromo-4,5-dimethoxyphenyl)-4H-chromen-7-ylcarbamoyl)ethylcarbamate

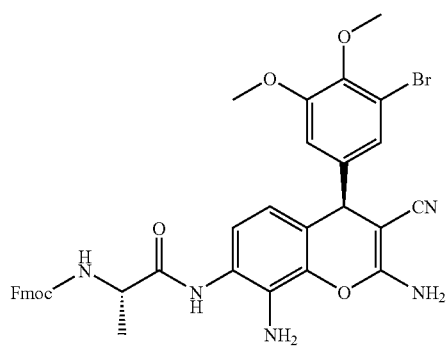

To an oven-dried carousel reaction flask charged with a magnetic stir bar at room temperature under argon was added (R)-2,7,8-triamino-3-cyano-4-(3-bromo-4,5-dimethoxyphenyl)-4H-chromene (0.200 g, 0.479 mmol), Fmoc-Ala-OH (0.179 g, 0.575 mmol), dimethylformamide (2.4 mL), HOBt 0.084 g, 0.62 mmol) and 1-ethyl-3-(3-dimethylaminopropyl)-carbodiimide (EDC) (0.119 g, 0.623 mmol). The black solution was stirred at room temperature overnight. The solution was diluted with EtOAc (50 mL), washed with water (3×30 mL), brine (10 mL), dried over MgSO$_4$, filtered and concentrated to give the crude product as a brown residue. Purification by flash column chromatography (silica gel 12 g pre-packed column, gradient elution with EtOAc:Hexanes, 1:9 to 1:4 to 1:1) gave 0.046 g (13%) of the title compound as a yellow solid: mp: 212-217° C. (dec); $^1$H-NMR (DMSO-d$_6$): δ 9.37 (br s, 1H), 7.89 (d, J=7.7 Hz, 2H), 7.76-7.69 (m, 3H), 7.44-7.39 (m, 2H), 7.35-7.30 (m, 2H), 6.98 (d, J=1.9 Hz, 1H), 6.88 (br s, 2H), 6.88 (d, J=8.0 Hz, 1H), 6.86 (d, J=1.9 Hz, 1H), 6.31 (d, J=8.3 Hz, 1H), 4.79 (br s, 2H), 4.69 (s, 1H), 4.31-4.23 (m, 4H), 3.80 (s, 3H), 3.70 (s, 3H), 1.32 (d, J=6.9 Hz, 3H).

EXAMPLE 4

Synthesis of (2S)-2-Amino-N—((R)-2,8-diamino-4-(3-bromo-4,5-dimethoxyphenyl)-3-cyano-4H-chromen-7-yl)propanamide

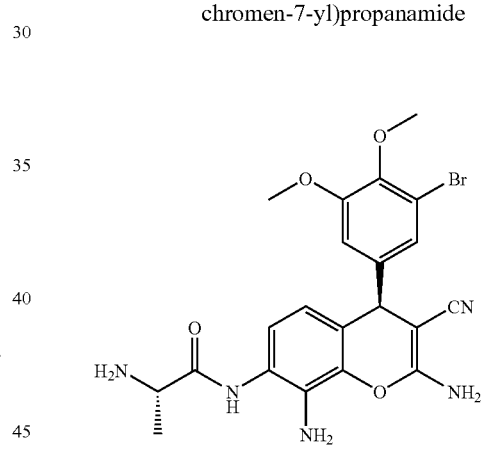

To an oven-dried one-neck round bottom reaction flask charged with a magnetic stir bar at room temperature under argon was added (9H-fluoren-9-yl)methyl(S)-1-((R)-2,8-diamino-3-cyano-4-(3-bromo-4,5-dimethoxyphenyl)-4H-chromen-7-ylcarbamoyl)-ethylcarbamate (0.045 g, 0.063 mmol), CH$_2$Cl$_2$:MeOH, 1:1 (2.11 mL) and 2N NaOH (0.063 mL, 0.13 mmol). The orange suspension was stirred at room temperature overnight. The suspension was concentrated leaving a brown residue. The residue was extracted with CHCl$_3$ (3×40 mL), dried over MgSO$_4$, filtered and concentrated to give the crude product. Purification by flash column chromatography (silica gel 4 g pre-packed column, elution with CH$_2$Cl$_2$:MeOH, 1:1) gave 0.005 g (16%) of the title compound as a yellow solid: $^1$H-NMR (DMSO-d$_6$): δ 8.32 (s, 1H), 7.02 (d, J=8.2 Hz, 1H), 6.98 (d, J=1.9 Hz, 1H), 6.91 (br s, 2H), 6.86 (d, J=1.9 Hz, 1H), 6.33 (d, J=8.5 Hz, 1H), 4.78 (br s, 2H), 4.69 (s, 1H), 3.80 (s, 3H), 3.70 (s, 3H), 1.22 (d, J=6.9 Hz, 3H). ESI-MS (C$_{21}$H$_{22}$BrN$_5$O$_4$) 487.09 m/z (%): 488 [M+H]$^+$ (100%), 490 [M+H]$^+$ (90%).

EXAMPLE 5

Synthesis of (9H-fluoren-9-yl)methyl((R)-2,8-diamino-4-(3-bromo-4,5-dimethoxyphenyl)-3-cyano-4H-chromen-7-ylcarbamoyl)methylcarbamate

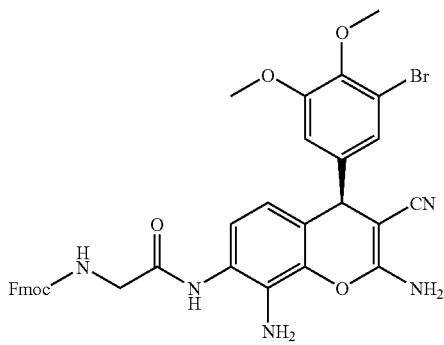

To an oven-dried carousel reaction flask charged with a magnetic stir bar at rt under argon was added (R)-2,7,8-triamino-3-cyano-4-(3-bromo-4,5-dimethoxyphenyl)-4H-chromene (0.500 g, 1.19 mmol), Fmoc-Gly-OH (0.427 g, 1.44 mmol), dimethylformamide (6.0 mL), HOBt (0.210 g, 1.56 mmol) and EDC (0.299 g, 1.56 mmol). The black solution was stirred at rt overnight. The solution was diluted with EtOAc (100 mL), washed with water (5×25 mL), brine (20 mL), dried over MgSO$_4$, filtered and concentrated to give the crude product as an orange solid. Purification by flash column chromatography (silica gel 20 g pre-packed column, gradient elution with EtOAc:Hexanes, 1:1 to 2:1) gave 0.125 g (15%) of the title compound as a yellow solid: mp: 128-130° C.; $^1$H-NMR (DMSO-d$_6$): 9.28 (br s, 1H), 7.90 (d, J=7.1 Hz, 2H), 7.72 (d, J=7.1 Hz, 2H), 7.62 (m, 1H), 7.42 (t, J=7.3 Hz, 2H), 7.33 (t, J=7.0 Hz, 2H), 6.99 (s, 1H), 6.92-6.87 (m, 2H), 6.89 (br s, 2H), 6.31 (d, J=8.2 Hz, 1H), 4.85 (br s, 2H), 4.69 (s, 1H), 4.32-4.25 (m, 3H), 3.84 (m, 2H), 3.80 (s, 3H), 3.70 (s, 3H).

EXAMPLE 6

2-Amino-N—((R)-2,8-diamino-4-(3-bromo-4,5-dimethoxyphenyl)-3-cyano-4H-chromen-7-yl)acetamide

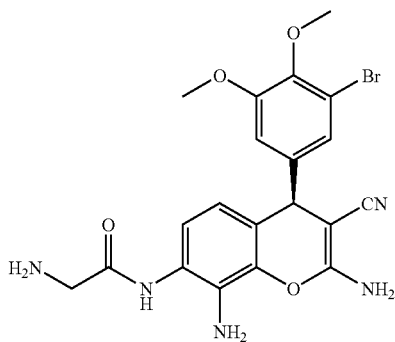

To an oven-dried one-neck round bottom reaction flask charged with a magnetic stir bar at rt under argon was added (9H-fluoren-9-yl)methyl((R)-2,8-diamino-4-(3-bromo-4,5-dimethoxyphenyl)-3-cyano-4H-chromen-7-ylcarbamoyl)methylcarbamate (0.050 g, 0.072 mmol), CH$_2$Cl$_2$:MeOH, 1:1 (2.40 mL) and 2N NaOH (0.072 mL, 0.14 mmol). The orange suspension was stirred at rt overnight. The suspension was concentrated leaving a brown residue. The residue was extracted with CHCl$_3$ (3×40 mL), dried over MgSO$_4$, filtered and concentrated to give the crude product. Purification by flash column chromatography (silica gel 4 g pre-packed column, gradient elution with CH$_2$Cl$_2$:MeOH, 96:4 to 90:10 with trace Et$_3$N) gave 0.012 g (35%) of the title compound as a yellow solid: $^1$H-NMR (CDCl$_3$): 9.34 (br s, 1H), 6.90 (d, J=1.9 Hz, 1H), 6.89 (d, J=8.5 Hz, 1H), 6.71 (d, J=1.9 Hz, 1H), 6.37 (d, J=8.2 Hz, 1H), 4.72 (br s, 2H), 4.64 (s, 1H), 4.29 (br s, 2H), 3.84 (s, 3H), 3.83 (s, 3H), 3.54 (br s, 2H).

EXAMPLE 7

Identification of (R)(−)-2,7,8-triamino-4-(3-bromo-4,5-dimethoxy-phenyl)-3-cyano-4H-chromene (1R) as a Caspase Cascade Activator and Inducer of Apoptosis in Solid Tumor Cells Human breast cancer cell lines T-47D and ZR-75-1, human colon cancer cell line DLD-1 and human non-small cell lung cancer cell line H1299 were grown according to media component mixtures designated by American Type Culture Collection+10% FCS (Invitrogen Corporation), in a 5% CO$_2$–95% humidity incubator at 37° C. T-47D and ZR-75-1 cells were maintained at a cell density between 30 and 80% confluency at a cell density of 0.1 to 0.6×10$^6$ cells/mL. Cells were harvested at 600×g and resuspended at 0.65×10$^6$ cells/mL into appropriate media+10% FCS. An aliquot of 45 µl of cells was added to a well of a 96-well microtiter plate containing 5 µl of a 10% DMSO in RPMI-1640 media solution containing about 0.16 to 10 µM of 2,7,8-triamino-4-(3-bromo-4,5-dimethoxy-phenyl)-3-cyano-4H-chromene (1) or other test compounds (0.016 to 1 µM final). An aliquot of 45 µl of cells was added to a well of a 96-well microtiter plate containing 5 µl of a 10% DMSO in RPMI-1640 media solution without test compound as the control sample. The samples were mixed by agitation and then incubated at 37° C. for 24 h in a 5% CO$_2$–95% humidity incubator. After incubation, the samples were removed from the incubator and 50 µl of a solution containing 20 µM of N-(Ac-DEVD)-N'-ethoxycarbonyl-R110 (SEQ ID No:1) fluorogenic substrate (Cytovia, Inc.; U.S. Pat. No. 6,335,429), 20% sucrose (Sigma), 20 mM DTT (Sigma), 200 mM NaCl (Sigma), 40 mM Na PIPES buffer pH 7.2 (Sigma), and 500 µg/ml lysolecithin (Calbiochem) was added. The samples were mixed by agitation and incubated at room temperature. Using a fluorescent plate reader (Model 1420 Wallac Instruments), an initial reading (T=0) was made about 1-2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

RFU$_{(T=3h)}$−Control RFU$_{(T=0)}$=Net RFU$_{(T=3h)}$

The activity of caspase cascade activation was determined by the ratio of the net RFU value for 2,7,8-triamino-4-(3-bromo-4,5-dimethoxy-phenyl)-3-cyano-4H-chromene or other test compound to that of control samples. The EC$_{50}$ (nM) was determined by a sigmoidal dose-response calculation (Prism 2.0, GraphPad Software Inc.). The caspase activation potency (EC$_{50}$) are summarized in Table I:

TABLE I
| Compound # | Structure | Caspase activation potency EC50 (nM) | | | |
|---|---|---|---|---|---|
| | | T47D | ZR751 | DLD-1 | H1299 |
| 1 | 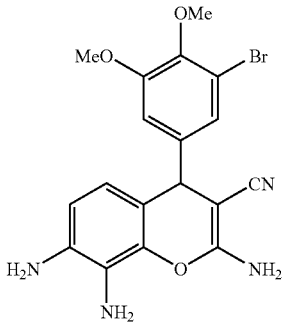 | 42 | 35 | 78 | 120 |
| 1R(−) | 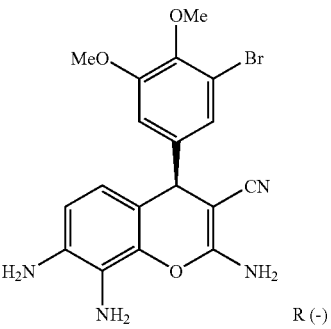 R (−) | 21 | 19 | 57 | 62 |
| 1S(+) | 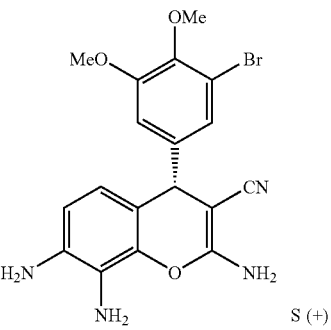 S (+) | 2489 | 2006 | 4571 | 3206 |
| 3 | 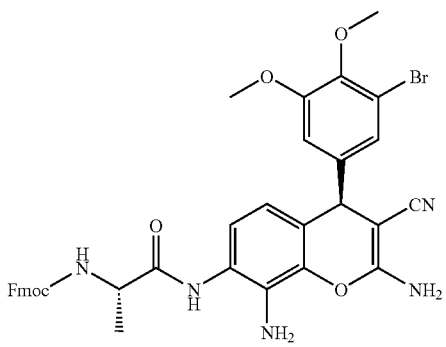 | 2880 | ND | ND | ND |

TABLE I-continued

| | | Caspase activation potency | | | |
|---|---|---|---|---|---|
| Compound | | EC50 (nM) | | | |
| # | Structure | T47D | ZR751 | DLD-1 | H1299 |
| 4 | | 52 | ND | ND | ND |
| 5 | | 2436 | ND | ND | ND |
| 6 | | 60 | ND | ND | ND |
| A | | 2541 | | | 3341 |

TABLE I-continued

Caspase activation potency

| Compound # | Structure | EC50 (nM) T47D | ZR751 | DLD-1 | H1299 |
|---|---|---|---|---|---|
| B | (structure) | 5503 | | | 5778 |
| C | (structure) | 160 | | | 273 |
| D | (structure) | >10000 | | | >10000 |
| E | (structure) | 3903 | | | 5334 |

TABLE I-continued

Caspase activation potency

| Compound # | Structure | EC50 (nM) | | | |
|---|---|---|---|---|---|
| | | T47D | ZR751 | DLD-1 | H1299 |
| F | *[chemical structure]* | | 4121 | | 5674 |
| G | *[chemical structure]* | | 1421 | | 3750 |

Thus, R(−)-2,7,8-triamino-4-(3-bromo-4,5-dimethoxy-phenyl)-3-cyano-4H-chromene (1R) is a potent caspase cascade activator and inducer of apoptosis in solid tumor cells, and is the active isomer of the racemate 2,7,8-triamino-4-(3-bromo-4,5-dimethoxy-phenyl)-3-cyano-4H-chromene. S(+)-2,7,8-triamino-4-(3-bromo-4,5-dimethoxy-phenyl)-3-cyano-4H-chromene (1S) is the inactive isomer of the racemate 2,7,8-triamino-4-(3-bromo-4,5-dimethoxy-phenyl)-3-cyano-4H-chromene. The observed activity of 1S might be due to the presence of small percent (~1%) of 1R in the sample tested. Compound 4, the alanine amide prodrug of 1R, also is a potent caspase cascade activator and inducer of apoptosis.

EXAMPLE 8

Identification of R(−)-2,7,8-triamino-4-(3-bromo-4,5-dimethoxy-phenyl)-3-cyano-4H-chromene (1R) As Antineoplastic Compound That Inhibits Cell Proliferation ($GI_{50}$)

Human breast cancer cells MX-1 and MDAMB435, hepatocarcinoma cells SNU398, colon cancer cells HCT116 and HeLa cells were grown and harvested as in Example 7. An aliquot of 90 μL of cells ($4.4 \times 10^4$ cells/mL) was added to a well of a 96-well microtiter plate containing 5 μL of a 10% DMSO in RPMI-1640 media solution containing 10 nM to 100 μM of R(−)-2,7,8-triamino-4-(3-bromo-4,5-dimethoxy-phenyl)-3-cyano-4H-chromene (1 nM to 10 μM final). An aliquot of 45 μL of cells was added to a well of a 96-well microtiter plate containing 5 μL of a 10% DMSO in RPMI-1640 media solution without compound as the control sample for maximal cell proliferation ($L_{Max}$). The samples were mixed by agitation and then incubated at 37° C. for 72 h in a 5% $CO_2$–95% humidity incubator. After incubation, the samples were removed from the incubator and 25 μL of CellTiter-Glo™ reagent (Promega) was added. The samples were mixed by agitation and incubated at room temperature for 10-15 min. Plates were then read using a luminescent plate reader (Model SPECTRAfluor Plus, Tecan) to give $L_{test}$ values.

Baseline for $GI_{50}$ (dose for 50% inhibition of cell proliferation) of initial cell numbers was determined by adding an aliquot of 45 μL of cells or 45 μL of media, respectively, to wells of a 96-well microtiter plate containing 5 μL of a 10% DMSO in RPMI-1640 media solution. The samples were mixed by agitation and then incubated at 37° C. for 0.5 h in a 5% $CO_2$–95% humidity incubator. After incubation, the samples were removed from the incubator and 25 μL of CellTiter-Glo™ reagent (Promega) was added. The samples were mixed by agitation and incubated at 37° C. for 10-15 min at room temperature in a 5% $CO_2$–95% humidity incubator. Fluorescence was read as above, ($L_{Start}$) defining luminescence for initial cell number used as baseline in $GI_{50}$ determinations.

Calculation:

$GI_{50}$ (dose for 50% inhibition of cell proliferation) is the concentration where $$[(L_{Test} - L_{Start})/(L_{Max} - L_{Start})] = 0.5.$$

The GI$_{50}$ (nM) are summarized in Table II:

TABLE II

| | GI$_{50}$ in Cancer Cells | | | | |
|---|---|---|---|---|---|
| | | GI$_{50}$ (nM) | | | |
| Example | MX1 | Hela | MDAMB435 | Snu398 | HCT116 |
| 1R | 17 | 25 | 9 | 28 | 19 |

Thus, R(−)-2,7,8-triamino-4-(3-bromo-4,5-dimethoxyphenyl)-3-cyano-4H-chromene is identified as antineoplastic compound that inhibits cell proliferation.

EXAMPLE 9

In Vitro Antivascular Activity of R(−)-2,7,8-triamino-4-(3-bromo-4,5-dimethoxy-phenyl)-3-cyano-4H-chromene (1R) in a HUVEC Tube Disruption Assay Aliquots of Matrigel basement membrane matrix (300 μl, BD Biosciences, Mississauga, Ontario, Canada) were added to each well of 24-well plates (Fisher Scientific Ltd, Nepean, Ontario, Canada) and allowed to incubate for 1 h at 37° C. HUVEC cells (3×10$^4$) were added per well in EGM-2 and incubated for 4 h at 37° C. in a 5% CO$_2$ atmosphere to allow the cells to form tube-like structures. Compound 1R was diluted in DMSO to its respective concentrations, added to cells, and allowed to incubate for 1 h at 37° C. in a 5% CO$_2$ atmosphere. Following the incubation, the medium was gently aspirated and fresh EGM-2 was added and cells were further incubated for 24 h. Miroscopy images were recorded with a Zeiss LSM 510 confocal microscope (Zeiss Canada Ltd, Toronto, Ontario, Canada). The effect of compound 1R on capillary tube disruption was evaluated by light microscopy (×40 magnification) and the results are summarized in Table III.

TABLE III

| Inhibition of tube formation by compound 1R | | | | |
|---|---|---|---|---|
| | Tube formation % inhibition | | | |
| Compound # | 3.3 nM | 10 nM | 30 nM | 100 nM |
| 1R | No inhibition | 75 | 100 | 100 |

Thus, (R)(−)-2,7,8-triamino-4-(3-bromo-4,5-dimethoxyphenyl)-3-cyano-4H-chromene (1R) inhibited tube formation at concentration as low as 10 nM, indicating that compound 1R has high antivascular activity.

EXAMPLE 10

Formulation of R(−)-2,7,8-triamino-4-(3-bromo-4,5-dimethoxy-phenyl)-3-cyano-4H-chromene (1R)

Compound 1R was prepared as a 10 mg/mL solution with 25% PEG 400(v/v), 5% Lutrol (w/v) in saline. A solution of 6.67% Lutrol in saline was prepared by adding 933 μL of saline into a vial containing 66.7 mg of Lutrol, and mixed until the Lutrol dissolved in the saline. A solution of 40 mg/mL compound 1R in PEG 400 was prepared by adding 973 μL of PEG 400 into a vial containing 40 mg of compound 1R, vortexed and the vial was placed on shaker or rotator until 1R was dissolved in PEG 400. The mixture can be heated occasionally to 50° C. to facilitate dissolution if needed. A solution of 10 mg/mL compound 1R in 25% PEG 400 (v/v), 5% Lutrol (w/v) in saline was prepared by pipetting 750 μL of 6.67% Lutrol in saline into a vial containing 250 μL of 40 mg/mL compound 1R in PEG 400, mixing while adding the saline solution. The solution was passed through 0.2 μm filter before injection.

Compound 1R also can be formulated as a 10 mg/mL solution in 7% PEG400/9% Tween80/84% D5W, and used for IV injection. Compound 1R also can be formulated as a 10 mg/mL solution in 10% cremophor/10% ethanol/80% saline, and used for IV injection.

EXAMPLE 11

In Vivo Anticancer Activity of (R)(−)-2,7,8-triamino-4-(3-bromo-4,5-dimethoxy-phenyl)-3-cyano-4H-chromene (1R)

MX1 human breast cancer tumors were obtained from the NCI-FCRDC and maintained as tumors in nude mice. Tumor bits were implanted with a trocar into the right mammary area of female nu/nu mice and allowed to grow to an average size of 200-250 mg, about 12 days after being implanted. Animals were randomized and assigned to study groups of 8-10 animals/group. Body weight were determined and tumor size were measured by calipers and converted to volume by the standard formula of Vol=L×W$^2$/2. Compound 1R was formulated in 7% PEG400/9% Tween80/84% D5W and administered IV via the tail vein at the indicated days and doses. Day 1 of the study was the first day of treatment. Survival time was the number of days for the tumor to reach 1000 mg or death, whichever occurred earliest. Median survival is the median for the group.

TABLE IV

| In vivo antitumor activity of compound 1R in MX-1 model | | | |
|---|---|---|---|
| | Median survival time (days) | | |
| Scheme | Once a day for days 1-5 (QD × 5) | Once a day for days 1-3 (QD × 3) | Once a week, day 1, 8, 15 (QW × 3) |
| Vehicle | 9.5 | 7 | 10 |
| 20 mg/kg | 46 | 19 | 27.5 |
| 40 mg/kg | >100 | 38 | 41 |
| 60 mg/kg | — | 78 | 37.5 |

Thus, (R)(−)-2,7,8-triamino-4-(3-bromo-4,5-dimethoxyphenyl)-3-cyano-4H-chromene (1R) increased the median survival time in the MX-1 model compared to vehicle control animals, indicating that compound 1R has high in vivo antitumor activity as a single agent.

EXAMPLE 12

Combination of (R)(−)-2,7,8-triamino-4-(3-bromo-4, 5-dimethoxy-phenyl)-3-cyano-4H-chromene (1R) with cisplatin and doxorubicin Mice implanted with MX1 human breast cancer tumors were treated with compound 1R as described in EXAMPLE 11. Cisplatin was administered IP whereas doxorubicin was administered IV at the indicated doses.

TABLE V

In vivo antitumor activity of compound 1R in combination with cisplatin and doxorubicin in MX-1 model

| | Median survival (days) | Number of tumor free mice at day 91 |
|---|---|---|
| Vehicle | 8.5 | 0 of 9 |
| Compound 1R, 40 mg/kg, day 1, 2, 3 (QD × 3), IV | 38.5 | 4 of 9 |
| Cisplatin, 2 mg/kg, day 2, IP | 11 | 0 of 9 |
| Compound 1R, 40 mg/kg, day 1, 2, 3 (QD × 3), IV, combined with cisplatin, 2 mg/kg, day 2, IP | >91 | 8 of 9 |
| Vehicle | 9 | 0 of 7 |
| Compound 1R, 40 mg/kg, day 1, 8, 15 (QW × 3), IV | 35 | 1 of 7 |
| Cisplatin, 2 mg/kg, day 2, 9, IP | 27 | 1 of 7 |
| Compound 1R, 40 mg/kg, day 1, 8, 15 (QW × 3), IV, combined with cisplatin, 2 mg/kg, day 2, 9, IP | >91 | 6 of 7 |
| Vehicle | 10.5 | 0 of 8 |
| Compound 1R, 40 mg/kg, day 1, 8, 15 (QW × 3), IV | 40 | 1 of 8 |
| Doxorubicin, 2 mg/kg, day 2, 9, IV | 11 | 0 of 9 |
| Compound 1R, 40 mg/kg, day 1, 8, 15 (QW × 3), IV, combined with doxorubicin, 2 mg/kg, day 2, 9, IV | 80.5 | 4 of 8 |

Thus, combination of (R)(−)-2,7,8-triamino-4-(3-bromo-4,5-dimethoxy-phenyl)-3-cyano-4H-chromene (1R) with cisplatin or doxorubicin significantly increased the median survival time of mice, and the number of tumor free animals in MX-1 model, indicating that compound 1R has superior activity when combined with other anticancer agents.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound of Formula 1R, substantially free from the corresponding (S)-stereoisomer:

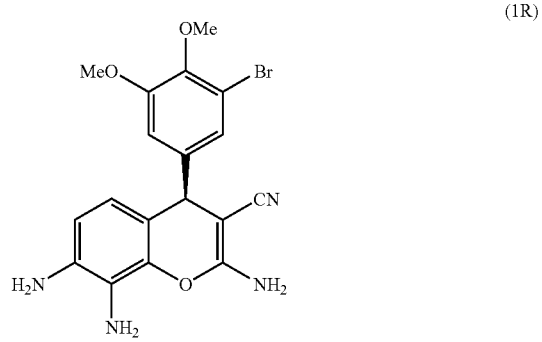

(1R)

or a pharmaceutically acceptable salt thereof.

2. The compound of claim 1, wherein said compound 1R is about 99.9% free from the corresponding (S)-stereoisomer.

3. An amide of a compound of Formula 1R, substantially free from the corresponding (S)-stereoisomer:

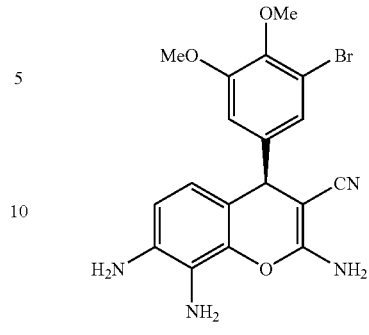

(1R)

wherein said compound is:
an amide of an amino acid.

4. The compound of claim 3, wherein said amino acid is selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

5. A pharmaceutical composition comprising the compound of claim 1, or a pharmaceutically acceptable salt thereof, and a pharmaceutically acceptable excipient or carrier.

6. The pharmaceutical composition of claim 5, comprising about 0.01 to about 50 mg/mL of the compound of claim 1.

7. The pharmaceutical composition of claim 5, wherein said excipient or carrier is selected from the group consisting of poly(ethylene glycol), block copolymers of poly(ethylene glycol) and poly(propylene glycol), and saline.

8. The pharmaceutical composition of claim 7, wherein said poly(ethylene glycol) is PEG 200, 400, 600, 800 or 1000.

9. The pharmaceutical composition of claim 7, comprising about 10 mg/mL of the compound of claim 1, about 25% (v/v) poly(ethylene glycol), about 5% (v/v) block copolymers of poly(ethylene glycol) and poly(propylene glycol) and saline.

10. The pharmaceutical composition of claim 5, wherein said excipient or carrier is selected from the group consisting of poly(ethylene glycol), polysorbate, and a solution of 5% dextrose in water.

11. The pharmaceutical composition of claim 10, wherein said polysorbate is polysorbate 20, 80, 81, 90 or 94.

12. The pharmaceutical composition of claim 11, comprising about 10 mg/mL of the compound of claim 1, about 7% (v/v) poly(ethylene glycol) 400, about 9% (v/v) polysorbate 80 and about 84% (v/v) of a solution of 5% dextrose in water.

13. The pharmaceutical composition of claim 5, wherein compound 1R is about 99% or greater free from the corresponding (S)-stereoisomer.

14. The pharmaceutical composition of claim 13, wherein compound 1R is about 99.9% free from the corresponding (S)-stereoisomer.

15. The pharmaceutical composition of claim 5, further comprising at least one known cancer chemotherapeutic agent, or a pharmaceutically acceptable salt of said agent.

16. A method of treating a disorder, wherein the disorder is cancer comprising administering an effective amount of the compound of claim 1.

17. A method of treating a disorder, wherein the disorder is solid tumors comprising administering an effective amount of the compound of claim 1.

18. A method of treating a disorder, wherein the disorder is a disease caused by overgrowth of vasculature comprising administering an effective amount of the compound of claim 1.

19. A method of treating a disorder, wherein the disorder is ocular neovascularization comprising administering an effective amount of the compound of claim 1.

20. The method of any one of claims 16-19 wherein said compound is administered as part of a pharmaceutical composition comprising a pharmaceutically acceptable excipient or carrier.

21. The method of any one of claims 16-19 wherein said compound is administered together with a cancer chemotherapeutic agent.

22. The method of claim 21, wherein said disorder is renal cell cancer and said cancer chemotherapeutic agent is sunitinib.

23. The method of claim 21, wherein said disorder is liver cancer and said cancer chemotherapeutic agent is sorafenib.

24. The method of claim 21, wherein said disorder is non-small cell lung cancer and said cancer chemotherapeutic agent is carbotaxel or bevacuzimab.

25. The method of claim 21, wherein said disorder is ovarian cancer and said cancer chemotherapeutic agent is doxorubicin.

26. The method of claim 21, wherein said disorder is prostate cancer and said cancer chemotherapeutic agent is satraplatin.

27. The method of claim 21, wherein said disorder is colorectal cancer and said cancer chemotherapeutic agent is bevacuzimab.

28. A pharmaceutical composition comprising the compound of claim 3 and a pharmaceutically acceptable excipient or carrier.

29. The pharmaceutical composition of claim 28, comprising about 0.01 to about 50 mg/mL of the compound of claim 3.

30. The pharmaceutical composition of claim 28, wherein said excipient or carrier is selected from the group consisting of poly(ethylene glycol), block copolymers of poly(ethylene glycol) and poly(propylene glycol), and saline.

31. The pharmaceutical composition of claim 30, wherein said poly(ethylene glycol) is PEG 200, 400, 600, 800 or 1000.

32. The pharmaceutical composition of claim 30, comprising about 10 mg/mL of the compound of claim 3, about 25% (v/v) poly(ethylene glycol), about 5% (v/v) block copolymers of poly(ethylene glycol) and polypropylene glycol) and saline.

33. The pharmaceutical composition of claim 28, wherein said excipient or carrier is selected from the group consisting of poly(ethylene glycol), polysorbate, and a solution of 5% dextrose in water.

34. The pharmaceutical composition of claim 33, wherein said polysorbate is polysorbate 20, 80, 81, 90 or 94.

35. The pharmaceutical composition of claim 34, comprising about 10 mg/mL of the compound of claim 3, about 7% (v/v) poly(ethylene glycol) 400, about 9% (v/v) polysorbate 80 and about 84% (v/v) of a solution of 5% dextrose in water.

36. The pharmaceutical composition of claim 28, further comprising at least one known cancer chemotherapeutic agent, or a pharmaceutically acceptable salt of said agent.

* * * * *